US010870682B2

(12) United States Patent
Messer et al.

(10) Patent No.: US 10,870,682 B2
(45) Date of Patent: Dec. 22, 2020

(54) METHODS AND COMPOSITIONS FOR DENGUE VIRUS VACCINES

(71) Applicant: The University of North Carolina at Chapel Hill, Chapel Hill, NC (US)

(72) Inventors: William Messer, Portland, OR (US); Ralph Baric, Haw River, NC (US); Aravinda de Silva, Chapel Hill, NC (US); Boyd Yount, Hillsborough, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/105,346

(22) Filed: Aug. 20, 2018

(65) Prior Publication Data

US 2019/0225654 A1    Jul. 25, 2019

Related U.S. Application Data

(63) Continuation of application No. 14/392,127, filed as application No. PCT/US2014/044410 on Jun. 26, 2014, now Pat. No. 10,053,493.

(60) Provisional application No. 61/839,687, filed on Jun. 26, 2013.

(51) Int. Cl.
| | |
|---|---|
| *A61K 39/12* | (2006.01) |
| *C07K 14/005* | (2006.01) |
| *C07K 16/10* | (2006.01) |
| *C12N 7/00* | (2006.01) |
| *C07K 14/18* | (2006.01) |
| *A61K 39/00* | (2006.01) |

(52) U.S. Cl.
CPC ........ *C07K 14/005* (2013.01); *C07K 14/1825* (2013.01); *C07K 16/1081* (2013.01); *C12N 7/00* (2013.01); *A61K 39/00* (2013.01); *A61K 39/12* (2013.01); *C07K 2317/76* (2013.01); *C07K 2319/00* (2013.01); *C12N 2770/24122* (2013.01); *C12N 2770/24134* (2013.01); *Y02A 50/30* (2018.01)

(58) Field of Classification Search
CPC ...... C07K 14/1825; C12N 2770/24121; C12N 2770/24122; C12N 2770/24134; A61K 39/12
See application file for complete search history.

(56) References Cited

U.S. PATENT DOCUMENTS

| | | |
|---|---|---|
| 4,501,729 A | 2/1985 | Boucher et al. |
| 4,708,871 A | 11/1987 | Geysen |
| 7,862,829 B2 | 1/2011 | Johnston et al. |
| 2011/0059131 A1 | 3/2011 | Chang et al. |

FOREIGN PATENT DOCUMENTS

| | | |
|---|---|---|
| EA | 200700904 | 12/2007 |
| WO | 01/03729 | 1/2001 |
| WO | 2011/119716 | 9/2011 |
| WO | 2012/027473 | 3/2012 |
| WO | 2012/082073 | 6/2012 |
| WO | 2013059493 | 4/2013 |
| WO | 2013/151764 | 10/2013 |

OTHER PUBLICATIONS

Extended European Search Report corresponding to European Patent Application No. 19176621.1 (10 pages) (dated Nov. 19, 2019).
Bielefeldt-Ohmann et al. "Analysis of a recombinant dengue-2 virus-dengue-3 virus hybrid envelope protein expressed in a secretory baculovirus system" Journal of General Virology, 78:2723-2733 (1997).
Chambers et al. "Yellow Fever Virus/Dengue-2 Virus and Yellow Fever Virus/Dengue-4 Virus Chimeras: Biological Characterization, Immunogenicity, and Protection against Dengue Encephalitis in the Mouse Model" Journal of Virology, 77(6):3655-3668 (2003).
Chokephaibulkit et al. "Challenges for the formulation of a universal vaccine against dengue" Experimental Biology and Medicine, 238:566-578 (2013).
De Alwis et al. "Identification of human neutralizing antibodies that bind to complex epitopes on dengue virions" Proceedings of the National Academy of Sciences, 109(19):7439-7444 (2012).
Extended European Search Report corresponding to European Patent Application No. 14817079.8 (10 pages) (dated Jan. 17, 2017).
Gallichotte et al. "Epitope Addition and Ablation via Manipulation of a Dengue Virus Serotype 1 Infectious Clone" mSphere, 2(1):e00380-16 (pp. 1-11) (2017).
GenBank Accession No. DQ211652 "West Nile virus strain NY99, complete genome" NCBI (5 pages) (Jun. 7, 2006).
GenBank Accession No. JX503529 "Yellow fever virus strain YF/Vaccine/USA/Sanofi-Pasteur-17D-204/UF795AA/YFVax, complete genome" NCBI (5 pages) (Sep. 16, 2012).
GenBank Accession No. U14163 "Japanese encephalitis virus SA14 polyprotein mRNA, complete cds" NCBI (5 pages) (Sep. 13, 1994).
Geysen et al. "Use of peptide synthesis to probe viral antigens for epitopes to a resolution of a single amino acid" Proceedings of the National Academy of Sciences USA, 81:3998-4002 (1984).
Geysen et al. "A Priori Delineation of a Peptide Which Mimics a Discontinuous Antigenic Determinant" Molecular Immunology, 23(7):709-715 (1986).
Gromowski et al. "Characterization of an antigenic site that contains a dominant, type-specific neutralization determinant on the envelope protein domain III (ED3) of dengue 2 virus" Virology, 366:349-360 (2007).
Hopp et al. "Prediction of protein antigenic determinants from amino acid sequences" Proceedings of the National Academy of Sciences USA, 78(6):3824-3828 (1981).

(Continued)

*Primary Examiner* — Jeffrey S Parkin
(74) *Attorney, Agent, or Firm* — Myers Bigel, P.A.

(57) ABSTRACT

The present invention provides compositions and methods of use comprising a chimeric dengue virus E glycoprotein comprising a dengue virus E glycoprotein backbone, which comprises amino acid substitutions that introduce an epitope that is recognized by an antibody from a dengue virus serotype that is different from the dengue virus serotype of the dengue virus E glycoprotein backbone.

6 Claims, 7 Drawing Sheets

Specification includes a Sequence Listing.

(56) References Cited

OTHER PUBLICATIONS

International Preliminary Report on Patentability corresponding to International Patent Application No. PCT/US2014/044410 (6 pages) (dated Dec. 29, 2015).

International Search Report and the Written Opinion of the International Searching Authority corresponding to International Patent Application No. PCT/US2014/044410 (7 pages) (dated Oct. 23, 2014).

Kyte et al. "A Simple Method for Displaying the Hydropathic Character of a Protein" Journal of Molecular Biology, 157:105-132 (1982).

Lai et al. "Epitope Determinants of a Chimpanzee Dengue Virus Type 4 (DENV-4)-Neutralizing Antibody and Protection against Passively Transferred Humanized Antibody" Journal of Virology, 81(23):12766-12774 (2007).

Matsui et al. "Characterization of dengue complex-reactive epitopes on dengue 3 virus envelope protein domain III" Virology, 384:16-20 (2009).

Meloen et al. "Mimotopes: realization of an unlikely concept" Journal of Molecular Recognition, 13:352-359 (2000).

Messer et al. "Functional Transplant of a Dengue Virus Serotype 3 (DENV3)-Specific Human Monoclonal Antibody Epitope into DENV1" Journal of Virology, 90(10):5090-5097 (2016).

Pal et al. "Immunization with the Chlamydia trachomatis major outer membrane protein, using adjuvants developed for human vaccines, can induce partial protection in a mouse model against genital challenge" Vaccine, 24(6):766-775 (2006) (Abstract Only).

Raviprakash et al. "A chimeric tetravalent dengue DNA vaccine elicits neutralizing antibody to all four virus serotypes in rhesus macaques" Virology, 353:166-173 (2006).

Smith et al. "Persistence of Circulating Memory B Cell Clones with Potential for Dengue Virus Disease Enhancement for Decades following Infection" Journal of Virology, 86(5):2665-2675 (2012).

Srikiatkhachorn et al. "Immune correlates for dengue vaccine development" Expert Review of Vaccines, 15 (4):455-465 (2016).

Thomas, Stephen J. "The Necessity and Quandaries of Dengue Vaccine Development" The Journal of Infectious Diseases, 203:299-303 (2011).

Zidane et al. "Thermodynamic stability of domain III from the envelope protein of flaviviruses and its improvement by molecular design" Protein Engineering, Design & Selection, 26(6):389-399 (2013).

GenBank Accession No. ABF72434.1 "envelope glycoprotein, partial [Dengue virus]" NCBI (1 page) (Jun. 5, 2006).

FIG. 4A

DENV3-1F4 vs 1F4 (DV1 mAb)

- icWestPac'74
- 3001ic
- 3001-1F4E
- 3001-1F4R
- 3001-1F4S

OD 405 vs mAb 1F4 [ug/mL]

FIG. 4B

DENV3-1F4 vs 5J7 (DV3 mAb)

OD 405 vs mAb 5J7 [ug/mL]

METHODS AND COMPOSITIONS FOR DENGUE VIRUS VACCINES

STATEMENT OF PRIORITY

This application is a continuation application of U.S. patent application Ser. No. 14/392,127, filed Dec. 23, 2015 and issued on Aug. 21, 2018 as U.S. Pat. No. 10,053,493, which is a 35 U.S.C. § 371 national phase application of International Application Serial No. PCT/US2014/044410, filed Jun. 26, 2014, which claims the benefit, under 35 U.S.C. § 119(e), of U.S. Provisional Application Ser. No. 61/839,687, filed Jun. 26, 2013, the entire contents of each of which are incorporated by reference herein.

STATEMENT OF GOVERNMENT SUPPORT

This invention was made with government support under Grant No. U54 AI057157 awarded by the National Institutes of Health. The United States government has certain rights in the invention.

STATEMENT REGARDING ELECTRONIC FILING OF A SEQUENCE LISTING

A Sequence Listing in ASCII text format, submitted under 37 C.F. R. § 1.821, entitled 5470-671CT_ST25.txt, 42,409 bytes in size, generated on Aug. 10, 2018 and filed via EFS-Web, is provided in lieu of a paper copy. This Sequence Listing is incorporated by reference into the specification for its disclosures.

FIELD OF THE INVENTION

The present invention is directed to dengue virus vaccines that induce neutralizing antibodies against more than one dengue virus serotype from a single source.

BACKGROUND OF THE INVENTION

Dengue is a mosquito-borne flavivirus that is spreading at an unprecedented rate and has developed into a major health and economic burden in over 50 countries. Current DENV vaccines protecting against all four DENV serotypes must be delivered as a "tetravalent" formulation of four viruses or four recombinant proteins, each intended to confer protection against that serotype. The correct mix of serotypes in the tetravalent cocktail to achieve a balanced antibody response is not known, underscored by the recent failure of the most advanced tetravalent live attenuated chimeric virus to provide clinically meaningful protection in a large phase 2B trial in Thailand (Sabchareon A, et al., 2012). Viral interference is thought to contribute to failure as one or more virus serotypes out-compete the others. The DENV-1/3 and DENV 3/1 chimeric viruses are single viruses that present epitopes recognized by neutralizing antibodies from both DENV-1 and DENV-3 immune individuals. This indicates that single viruses should be able to elicit neutralizing antibodies targeting two serotypes at once, replacing two viruses (DENV-1 and 3) with one virus (DENV-1/3 or DENV-3/1).

BRIEF DESCRIPTION OF THE DRAWINGS

FIGS. 4A-B. For the DENV-3/1 mutants, the EDI-II hinge defined by the monoclonal antibody 1F4 footprint from DENV1 (WestPac '74) was transplanted into a DENV-3 background (3001) creating a DENV-1/3 hinge mutant. This transplant was executed for three different viruses, (1F4S, 1F4R, and 1F4E), with each variant representing a larger epitope region. The EDI-II hinge from rDENV-3 was put into a recombinant rDENV-1 virus. This figure shows enzyme linked immunosorbent assay (ELISA) data with relative binding of antibody by optical density (OD) on the Y-axis and increasing antibody concentration on the X-axis. A) Binding of mAb 1F4 to 3001-1F4S, R and E. The rising curve against the chimeric virus shows binding of the antibody, in contrast to parental 3001, which does not bind mAb 1F4. B) Binding of mAb 5J7 to parental 3001, 3001-1F4S, R and E. 5J7 binding is preserved in these viruses, whereas epitope donor icWestPac '74 does not bind 5J7.

SUMMARY OF THE INVENTION

Figure 1:
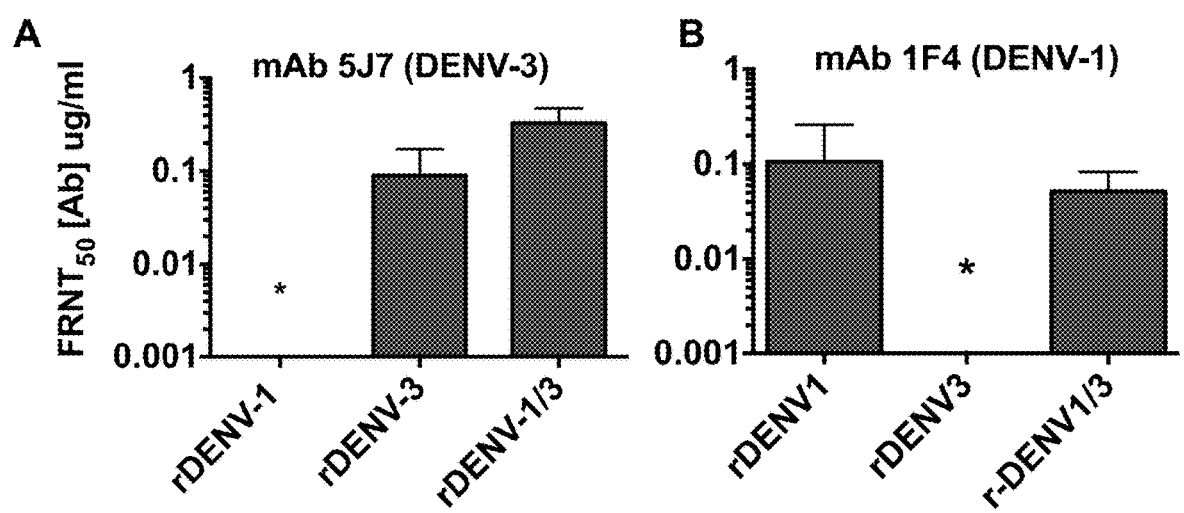
FIG. 1. For the DENV-1/3 mutant, the EDI-II hinge from DENV3 was transplanted into a DENV-1 background, WestPac'74, creating a DENV-3/1 hinge mutant. The EDI-II hinge was defined using the DENV3 specific human mAb 5J7. Panel A) The resultant virus, rDENV-1/3, was tested against monoclonal antibody 5J7. This figure shows that DENV-1 is not neutralized by 5J7, whereas DENV-3 is. rDENV-1/3, which only contains the DENV-3 EDI/II hinge, is neutralized by 5J7 at concentrations equivalent to DENV-3 neutralizing concentrations. This demonstrates successful transplant of the 5J7 epitope into DENV-1. Panel B) This panel shows that DENV-3 is not neutralized by mAb 1F4, DENV-1 is neutralized by 1F4, and rDENV-1/3 is also neutralized, indicating that 1F4 can still bind to and neutralize the chimeric virus.
Figure 2A:
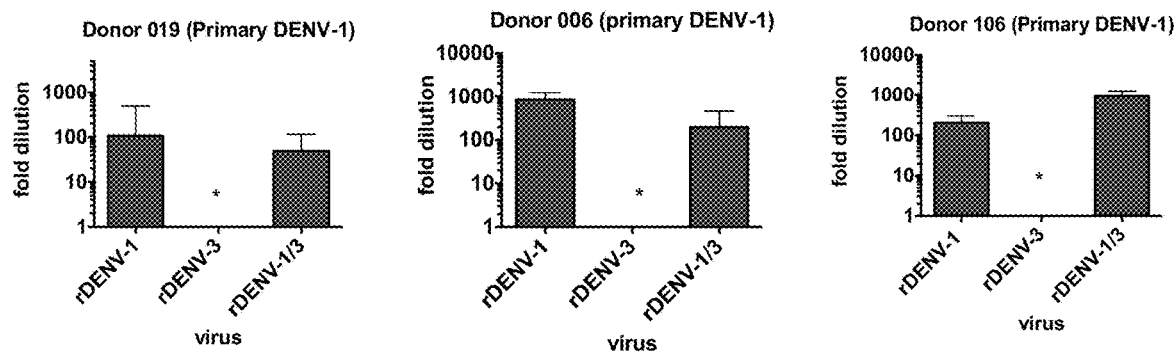
FIGS. 2A-B. This figure shows primary DENV-1 and DENV-3 human immune sera tested against DENV-1, DENV-3 and the hinge chimeric virus WestPac-3001 hinge (rDENV-1/3). The Y-axis shows fold dilution of immune sera required to neutralize 50% of input virus in tissue culture. The higher values indicate more potent serum. A) DENV-1 primary immune sera potently neutralizes DENV-1 but not DENV-3. rDENV-1/3 is sensitive to neutralization by DENV-1 immune sera at concentrations similar to DENV-1, indicating that in contrast to the parental DENV-3 virus, the chimeric virus displays epitopes recognized by DENV-1 immune sera. B) DENV-3 primary immune sera does not neutralize DENV-1 but neutralizes DENV-3. rDENV-1/3 is neutralized by DENV-3 primary immune sera at concentrations similar to DENV-3, indicating that the chimeric virus rDENV-1/3 preserves the critical DENV-3 epitopes targeted by DENV-3 antibodies in DENV-3 human immune sera. * indicates not neutralized.
Figure 2B:
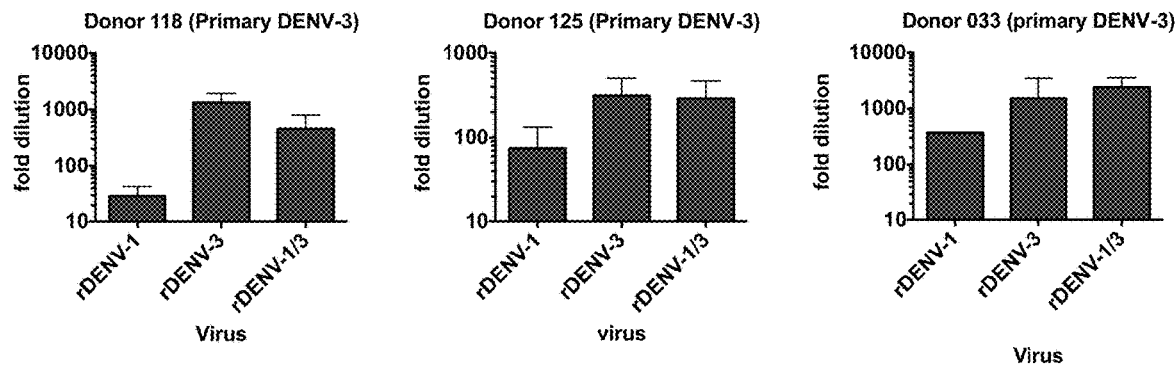
Figure 3:
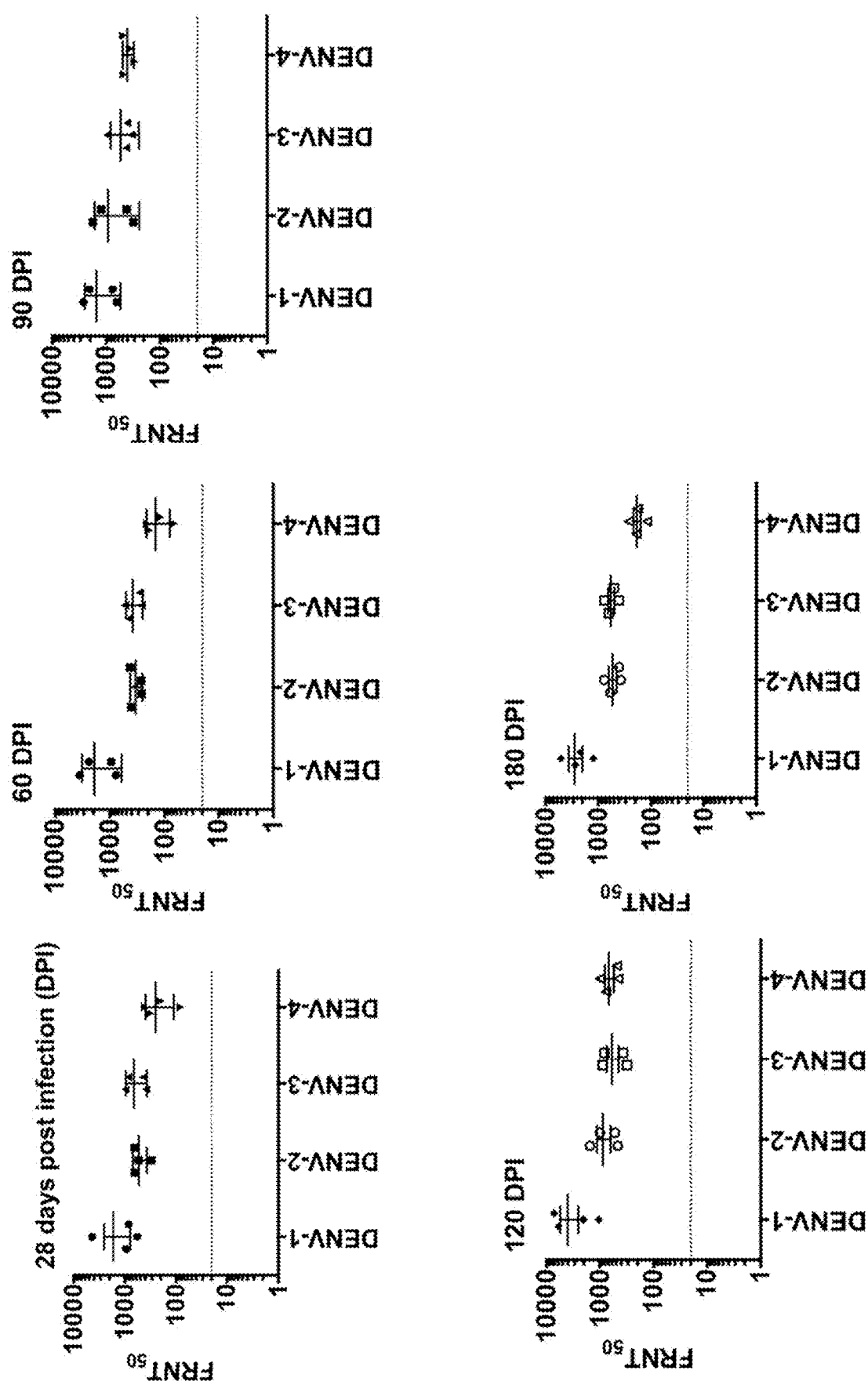
FIG. 3. This figure shows that WestPac'74 3001-hinge induces broadly cross-neutralizing antibodies at 28, 60, 90, 120 and 180 days post infection in rhesus macaques. The Y axis shows neutralizing antibody titer as above. The X axis shows each virus serotype. Each plotted point is the neutralizing titer for a single rhesus macaque against a given serotype. The central line through each cluster of points is the geometric mean neutralizing titer for each group of macaques against each serotype. The whiskers show standard error of the mean. Each time point (28, 30, 60, 90, 120, 180 days) shows broadly cross-neutralizing antibody responses against all four serotypes.
Figure 5A:
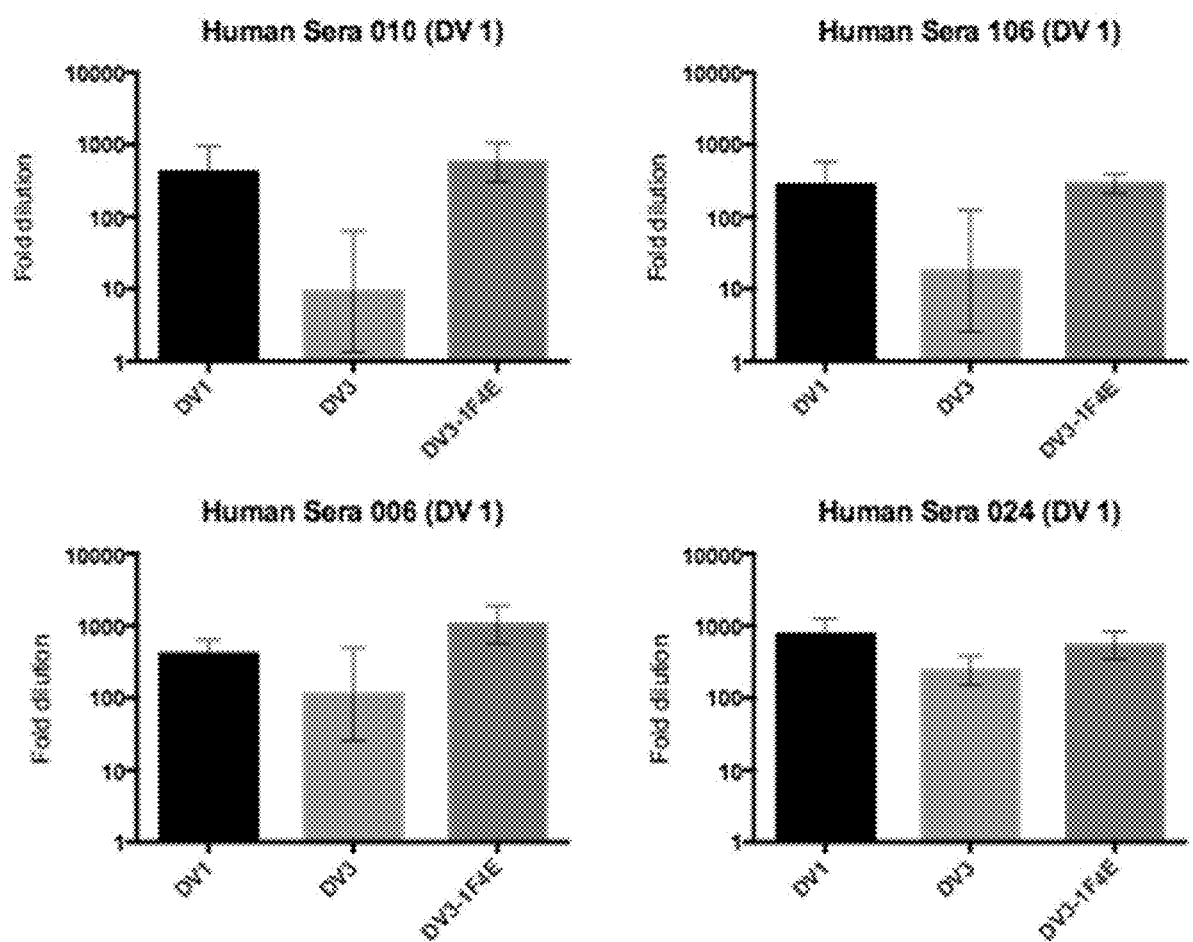
FIGS. 5A-B. This figure shows primary DENV-1 and DENV-3 human immune sera tested against DENV-1, DENV-3 and the hinge chimeric virus 3001-1F4E. The Y-axis shows fold dilution of immune sera required to neutralize 50% of input virus in tissue culture. The higher values indicate more potent serum. A) DENV-1 primary immune sera potently neutralizes DENV-1 but not DENV-3. 3001 1F4E is sensitive to neutralization by DENV-1 immune sera at concentrations similar to DENV-1, indicating that in contrast to the parental DENV-3 virus, the chimeric virus displays epitopes recognized by DENV-1 immune sera. B) DENV-3 primary immune sera does not neutralize DENV-1 but neutralizes DENV-3. 3001 1F4E is neutralized by DENV-3 primary immune sera at concentrations similar to DENV-3, indicating that the chimeric virus 3001-1F4E preserves the critical DENV-3 epitopes targeted by DENV-3 antibodies in DENV-3 human immune sera.
Figure 5B:
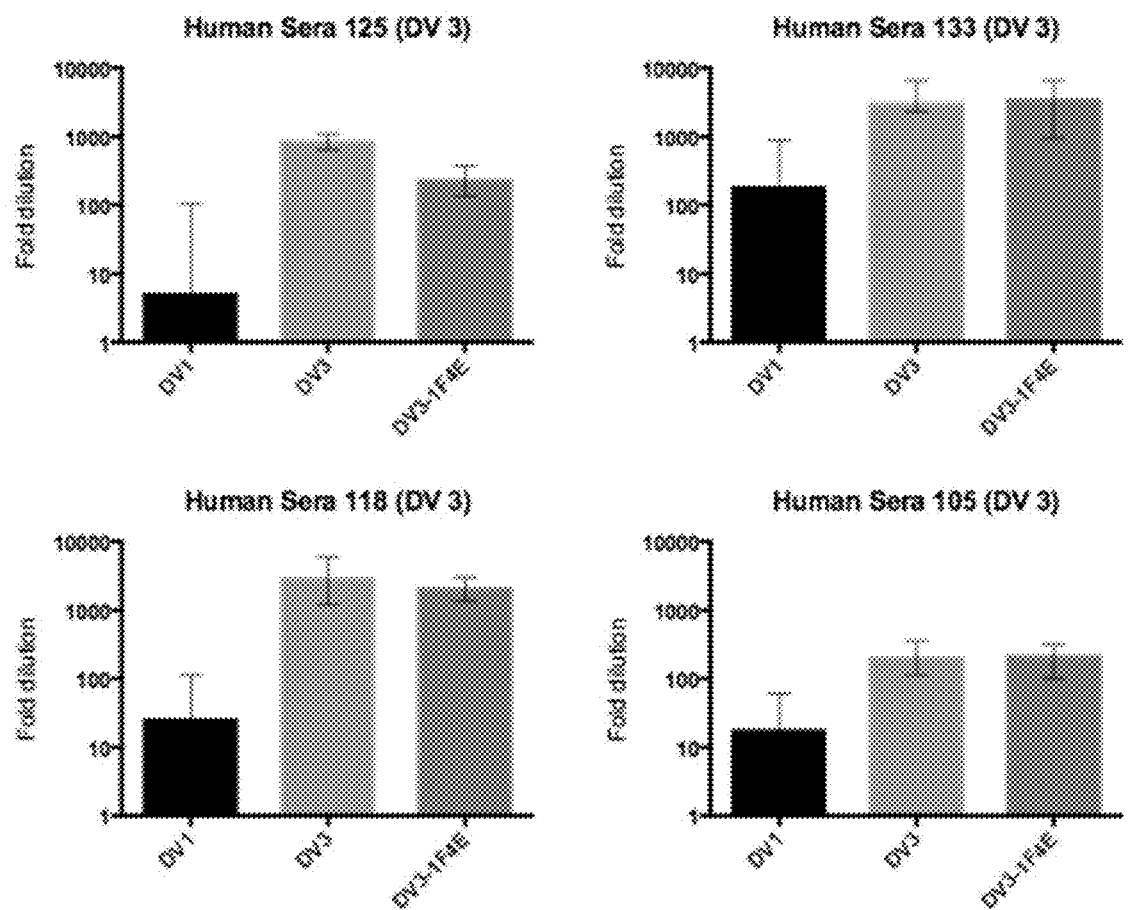
Figure 6:
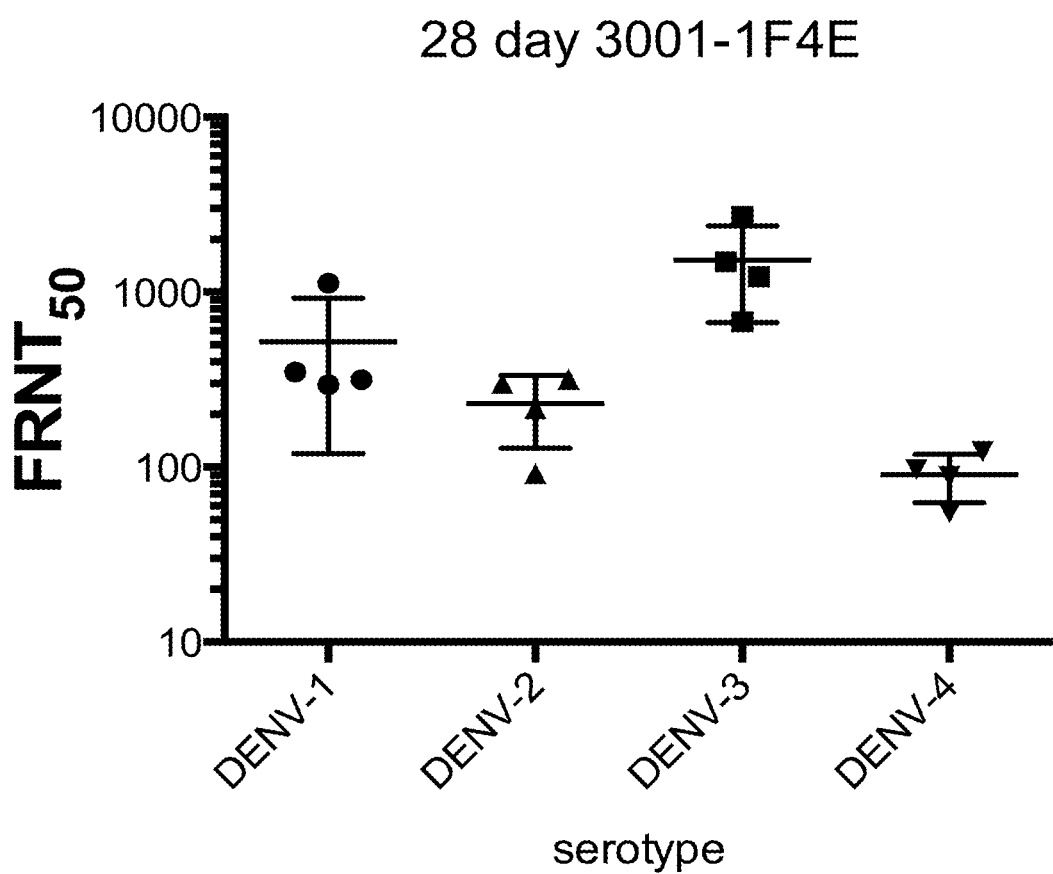
FIG. 6. Immunogenicity of 3001-1F4E in rhesus macaques. Only one time point is provided, showing broadly cross-neutralizing antibodies, consistent with what was found for WestPac-3001 hinge.

The present invention provides a chimeric dengue virus E glycoprotein comprising a dengue virus E glycoprotein backbone that comprises amino acid substitutions that introduce an epitope that is recognized by an antibody that is reactive with a dengue virus serotype that is different from the dengue virus serotype of the dengue virus E glycoprotein backbone. In one embodiment, the dengue virus E glycoprotein backbone is from dengue virus serotype 1 and in one embodiment, the dengue virus E glycoprotein backbone is from dengue virus serotype 3. In some embodiments, the antibody is reactive with dengue virus serotype 3 (e.g., monoclonal antibody 5J7) and in other embodiments, the antibody is reactive with dengue virus serotype 1 (e.g., monoclonal antibody 1F4).

The present invention further provides a chimeric dengue virus E glycoprotein, comprising the amino acid sequence:

(SEQ ID NO: 3)
MRCVGIGNRDFVEGLSGATWVDVVLEHGSCVTTMAKDKPTLDIELLKTEA

TQLATLRKLCIEAKISNTTTDSRCPTQGEATLVEEQDTNFVCRRTFVDRG

WGNGCGLFGKGSLITCAKFKCVTKIEGKVVQYENLKYSVIVTVHTGDQHQ

VGNETTEHGTIATITPQAPTSEIQLTDYGALTLDCSPRTGLDFNEMILLT

MKNKAWMVHRQWFLDLPLPWTSGASTSQETWNRQDLLVTFKTAHAKKQEV

VVLGSQEGAMHTALTGATEIQNSGGTSIFAGHLKCRLKMDKLTLKGMSYV

MCTGSFKLEKEVAETQHGTVLVQVKYEGTDAPCKIPFSSQDEKGVTQNGR

LITANPIVTDKEKPVNIEAEPPFGESYIVVGAGEKALKLSWFKKG

Also provided herein is a chimeric dengue virus E glycoprotein, comprising the amino acid sequence:

(SEQ ID NO: 4)
MRCVGIGNRDFVEGLSGATWVDVVLEHGGCVTTMAKNKPTLDIELFKTEV

TNPAVLRKLCIEGKITNITTDSRCPTQGEAVLPEEQDQNYVCKHTYVDRG

WGNGCGLFGKGSLVTCAKFQCLEPIEGKVVQYENLKYSVIVTVHTGDQHQ

VGNETTEHGTIATITPQAPTSEIQLTDYGALGLECSPRTGLDFNEMILLT

MKNKAWMVHRQWFFDLPLPWTSGATTETPTWNRKELLVTFKNAHAKKQEV

VVLGSQEGAMHTALTGATEIQTSGTTTIFAGHLKCRLKMDKLELKGMSYA

MCTNTFVLKKEVSETQHGTILIKVEYKGEDAPCKIPFSTEDGQGKAHNGR

LITANPVVTKKEEPVNIEAEPPFGESNIVIGIGDNALKINWYKKG

Additionally provided herein is flavivirus particle or virus like particle (VLP) comprising the E glycoprotein of this invention.

An isolated nucleic acid molecule encoding the E glycoprotein of this invention is also provided herein, as well as an isolated nucleic acid molecule encoding the flavivirus particle or VLP of this invention.

The present invention also provides a composition comprising the E glycoprotein of this invention in a pharmaceutically acceptable carrier and provides a composition comprising the nucleic acid molecule of this invention in a pharmaceutically acceptable carrier.

Furthermore, the present invention provides a method of producing an immune response to a dengue virus in a subject (e.g., a subject in need thereof), comprising administering to the subject an effective amount of the E glycoprotein of this invention, the flavivirus particle of this invention, the nucleic acid molecule of this invention and/or the composition of this invention and any combination thereof.

The present invention also provides a method of treating a dengue virus infection in a subject in need thereof, comprising administering to the subject an effective amount of the E glycoprotein of this invention, the flavivirus particle of this invention, the nucleic acid molecule of any of this invention and/or the composition of this invention and any combination thereof.

Additionally provided herein is a method of preventing a dengue virus infection in a subject (e.g., a subject in need thereof), comprising administering to the subject an effective amount of the E glycoprotein of this invention, the flavivirus particle of this invention, the nucleic acid molecule of any of this invention and/or the composition of this invention and any combination thereof.

A method is also provided herein of protecting a subject (e.g., a subject in need thereof), from the effects of dengue virus infection, comprising administering to the subject an effective amount of the E glycoprotein of this invention, the flavivirus particle of this invention, the nucleic acid molecule of any of this invention and/or the composition of this invention and any combination thereof.

The present invention further provides the E glycoprotein of this invention, the flavivirus particle of this invention, the nucleic acid molecule of this invention and/or the composition of this invention for use in the manufacture of a medicament for producing an immune response to a dengue virus in a subject, for treating a dengue virus infection in a subject in need thereof, for preventing a dengue virus infection in a subject and/or for protecting a subject from the effects of dengue virus infection.

Also provided herein is the use of the E glycoprotein of this invention, the flavivirus particle of this invention, the nucleic acid molecule of this invention and/or the composition of this invention for use in producing an immune response to a dengue virus in a subject, in treating a dengue virus infection in a subject in need thereof, in preventing a dengue virus infection in a subject and/or in protecting a subject from the effects of dengue virus infection.

DETAILED DESCRIPTION OF THE INVENTION

The present invention is based on the unexpected discovery that epitope regions that define a DENV serotype can be transferred into a protein backbone of a different DENV serotype to create a chimeric molecule that contains antibody targets for both serotypes, thereby functioning as a bivalent vaccine that can induce neutralizing antibodies against two different DENV serotypes from a single source. Thus, in one embodiment, the present invention provides a platform for construction of a chimeric dengue virus E glycoprotein backbone that comprises amino acid substitutions that introduce epitopes that are recognized by an antibody that is reactive with a dengue virus serotype that is different from the dengue virus serotype of the dengue virus E glycoprotein backbone.

In some embodiments, that dengue virus E glycoprotein backbone is from dengue virus serotype 1. In some embodiments, the dengue virus E glycoprotein backbone can be from dengue virus serotype 2, dengue virus serotype 3 or dengue virus serotype 4.

In some embodiments, the antibody that is reactive with a dengue virus serotype that is different from the dengue virus serotype of the dengue virus E glycoprotein backbone is an antibody that is reactive with dengue virus serotype 3. A nonlimiting example of such an antibody is monoclonal antibody 5J7.

In other embodiments, the antibody that is reactive with a dengue virus serotype that is different from the dengue virus serotype of the dengue virus E glycoprotein backbone is an antibody that is reactive with dengue virus serotype 1, dengue virus serotype 2 or dengue virus serotype 4.

It would be understood that any combination of a first dengue virus serotype for the dengue virus E glycoprotein backbone and a second dengue virus serotype that is the target of the antibody that recognizes the epitope introduced into the E glycoprotein backbone can be used, provided that the first dengue virus serotype and the second dengue virus serotype are different (i.e., not the same serotype).

In some embodiments, the chimeric dengue virus E glycoprotein of this invention can comprise, consist essentially of or consist of the amino acid sequence:

```
WestPac74-3001 hinge (rDENV-1/3)
                                        (SEQ ID NO: 3)
MRCVGIGNRDFVEGLSGATWVDVVLEHGSCVTTMAKDKPTLDIELLKTEA

TQLATLRKLCIEAKISNTTTDSRCPTQGEATLVEEQDTNFVCRRTFVDRG

WGNGCGLFGKGSLITCAKFKCVTKIEGKVVQYENLKYSVIVTVHTGDQHQ

VGNETTEHGTIATITPQAPTSEIQLTDYGALTLDCSPRTGLDFNEMILLT

MKNKAWMVHRQWFLDLPLPWTSGASTSQETWNRQDLLVTFKTAHAKKQEV

VVLGSQEGAMHTALTGATEIQNSGGTSIFAGHLKCRLKMDKLTLKGMSYV

MCTGSFKLEKEVAETQHGTVLVQVKYEGTDAPCKIPFSSQDEKGVTQNGR

LITANPIVTDKEKPVNIEAEPPFGESYIVVGAGEKALKLSWFKKG.
```

In some embodiments, the chimeric dengue virus E glycoprotein of this invention can comprise, consist essentially of or consist of the amino acid sequence:

```
3001-1F4E (rDENV-3/1)
                                        (SEQ ID NO: 4)
MRCVGIGNRDFVEGLSGATWVDVVLEHGGCVTTMAKNKPTLDIELFKTEV

TNPAVLRKLCIEGKITNITTDSRCPTQGEAVLPEEQDQNYVCKHTYVDRG

WGNGCGLFGKGSLVTCAKFQCLEPIEGKVVQYENLKYSVIVTVHTGDQHQ

VGNETTEHGTIATITPQAPTSEIQLTDYGALGLECSPRTGLDFNEMILLT

MKNKAWMVHRQWFFDLPLPWTSGATTETPTWNRKELLVTFKNAHAKKQEV

VVLGSQEGAMHTALTGATEIQTSGTTTIFAGHLKCRLKMDKLELKGMSYA

MCTNTFVLKKEVSETQHGTILIKVEYKGEDAPCKIPFSTEDGQGKAHNGR

LITANPVVTKKEEPVNIEAEPPFGESNIVIGIGDNALKINWYKKG
```

The present invention also provides a flavivirus particle or virus like particle (VLP) comprising the chimeric E glycoprotein of this invention.

Production of the chimeras of this invention can be carried out by introducing some (e.g., 1, 2, 3, 4, 5, 6, 7, 8, 9, 10, 11, 12, 13, 14, 15, etc.) or all of the amino acid substitutions identified in Table 1 into a dengue virus E glycoprotein backbone or flavivirus E glycoprotein backbone. Not every amino acid identified in Table 1 is required to be substituted to produce a chimeric protein of this invention. For example, in some embodiments further substitutions and/or omission of substitutions of about 1, 2, 3, 4 or 5 amino acids at either end of the contiguous amino acid sequences identified in Table 1 as the respective epitope regions can be included in production of a chimera of this invention. The number of substitutions necessary to produce the desired conformational epitope can be readily determined by one of ordinary skill in the art according to the teachings herein and according to protocols well known in the art. The amino acid position numbering in Table 1 is based on the amino acid sequence of WestPac74 (DENV-1), or the amino acid sequence of UNC 3001 (DENV-3), as provided herein. However it would be readily understood by one of ordinary skill in the art that the equivalent amino acid positions in other dengue virus E glycoprotein amino acid sequences or other flavivirus E glycoprotein amino acid sequences can be readily identified and employed in the production of the chimeric proteins of this invention.

Table 2 shows one example of modifications that can be made to the nucleotide sequence encoding the DENV-1 E glycoprotein to introduce the epitope that is recognized by the monoclonal antibody 5J7, which is reactive with DENV-3. The amino acid sequence that results from translation of a nucleotide sequence comprising these substitutions is:

```
                                        (SEQ ID NO: 3)
MRCVGIGNRDFVEGLSGATWVDVVLEHGSCVTTMAKDKPTLDIELLKTEA

TQLATLRKLCIEAKISNTTTDSRCPTQGEATLVEEQDTNFVCRRTFVDRG

WGNGCGLFGKGSLITCAKFKCVTKIEGKVVQYENLKYSVIVTVHTGDQHQ

VGNETTEHGTIATITPQAPTSEIQLTDYGALTLDCSPRTGLDFNEMILLT

MKNKAWMVHRQWFLDLPLPWTSGASTSQETWNRQDLLVTFKTAHAKKQEV

VVLGSQEGAMHTALTGATEIQNSGGTSIFAGHLKCRLKMDKLTLKGMSYV

MCTGSFKLEKEVAETQHGTVLVQVKYEGTDAPCKIPFSSQDEKGVTQNGR

LITANPIVTDKEKPVNIEAEPPFGESYIVVGAGEKALKLSWFKKG.
```

It would be understood that the modifications provided in Table 2 provide one example of how the amino acid sequence above can be obtained and that, due to the degeneracy of the amino acid codons, numerous other modifications can be made to the nucleotide sequence encoding the DENV-3 E glycoprotein to obtain this amino acid sequence.

Table 3 shows that WestPac'74 3001-hinge is infectious in rhesus macaques infected subcutaneously with 500,000 infectious units of virus. The reported values for each day are log transformed monkey serum virus titers quantified by immunofocus assay.

Table 4. Attenuation of 3001-1F4E in rhesus macaques. This table shows that 3001-1F4E is infectious in rhesus macaques infected subcutaneously with 500,000 infectious units of virus. However, this virus was below quantitative level of detection (50 infectious virus/mL serum). A more sensitive assay, the delayed focus assay, is capable of detecting virus<50 infectious units/mL, but is not capable of quantifying the low level of virus present. Consequently days for which virus was detected by our most sensitive assay are scored as positive with "+". Total number of days infected are shown in the left column. The low level of viremia and low mean number of days infected (2.25 days) are consistent with virus attenuation in macaques.

Table 5. To further characterize the chimeric virus DENV 1/3, it was probed with a DENV-1 specific monoclonal antibody, 1F4. 1F4 is serotype specific and its target epitope is in the EDI-II hinge. If the transplanted DENV-3 EDI-II hinge disrupts the 1F4 epitope, 1F4 should no longer neutralize the chimeric WestPac74/3001 virus.

In some embodiments, the present invention provides a chimeric flavivirus E glycoprotein in which amino acid substitutions are made to introduce a dengue virus epitope into a flavivirus E glycoprotein from a flavivirus that is not a dengue virus. Thus, in some embodiments, the present invention provides a flavivirus E glycoprotein comprising a chimeric E glycoprotein comprising a flavivirus E glycoprotein backbone that is not a dengue virus E glycoprotein backbone, wherein the flavivirus E glycoprotein backbone comprises amino acid substitutes that introduce an epitope that is recognized by an antibody that is reactive with a dengue virus.

Nonlimiting examples of flaviviruses that can be used include yellow fever virus (YFV) (e.g., GenBank® Database Accession No. JX503529) Japanese encephalitis virus (JEV) (e.g., GenBank® Database Accession No. U14163), West Nile virus (WNV) (e.g., GenBank® Database Accession No. DQ211652) and any other flavivirus now known or later identified.

It is known in the art that many attempts to produce dengue virus vaccines result in the production of non-neutralizing antibodies, which may increase the likelihood of pathology upon subsequence exposure to natural infection or vaccine. Another approach to provide an engineered epitope is to deliver all or a portion of the dengue virus E protein incorporated into another flavivirus particle or VLP. In representative embodiments, the heterologous flavivirus is West Nile virus or Yellow Fever virus. Portions of the E protein can be grafted into the E protein of the heterologous flavivirus backbone, e.g., to reduce the generation of non-neutralizing dengue virus antibodies to non-neutralizing epitopes present in the dengue virus E protein and/or other dengue virus structural proteins.

Thus, a chimeric flavivirus or chimeric flavivirus VLP can present the quaternary dengue virus epitope in proper conformation while reducing the generation of non-neutralizing antibodies to other portions of the dengue virus E protein and/or other structural proteins that are not presented in the chimeric flavivirus or flavivirus VLP.

In some embodiments of the invention the individual and conformational epitopes of the flavivirus E glycoprotein or dengue virus E glycoprotein can be presented on a synthetic backbone or support structure so that the epitopes within the synthetic backbone or support structure mimic the conformation and arrangement of the epitopes within the structure of the E glycoprotein, virus particle or VLP.

In still further embodiments of the invention, the present invention provides peptide mimitopes (see, Meloen et al. (2000) *J. Mol. Recognit.* 13, 352-359) that mimic the individual and conformational epitopes of the E glycoproteins of the invention. Mimitopes may be identified using any technique known in the art, such as by surface stimulation, random peptide libraries or phage display libraries, using an antibody or antibodies to the individual and conformational epitopes of the E glycoproteins of the invention.

The invention further provides a nucleic acid (e.g., isolated nucleic acid) encoding a dengue virus epitope or a polypeptide of the invention.

The invention further provides a nucleic acid (e.g., an isolated nucleic acid) encoding a chimeric flavivirus VLP or a chimeric flavivirus particle (e.g., a viral coat of the flavivirus particle) of the invention.

Also provided are vectors encoding the nucleic acids of the invention.

Also provided are cells comprising the vectors, nucleic acids, dengue virus epitopes, polypeptides, chimeric flavivirus VLPs or chimeric flavivirus particles of the invention.

The invention also provides immunogenic compositions comprising the cells, vectors, nucleic acids, dengue virus epitopes, polypeptides, chimeric flavivirus VLPs or chimeric flavivirus particles of the invention. In embodiments, the immunogenic composition is monovalent. In embodiments, the immunogenic composition is multivalent (e.g., tetravalent) for dengue virus serotypes DEN1, DEN2, DEN 3 and/or DEN4.

The invention encompasses methods of producing an immune response to a dengue virus in a subject, the method comprising administering to the subject an effective amount of a dengue virus epitope, a polypeptide, a chimeric flavivirus VLP or chimeric flavivirus particle, nucleic acid, vector, cell or immunogenic composition of the invention.

Further, the present invention can advantageously be practiced to induce an immune response against one, two, three or all four of DEN1, DEN2, DEN3 and DEN4. It is well-known in the art that effective and safe multivalent dengue vaccines have been a challenge to design because of the problem of interference among serotypes. For example, the immune response may be predominantly directed against only some of the target serotypes. Multiple vaccinations are then required to try to achieve a response against all serotypes; however, in the case of dengue virus, this approach can be dangerous because repeated administrations to a subject with pre-existing antibodies can lead to dengue hemorrhagic fever.

A still further aspect of the invention is a method of treating a dengue virus infection, comprising administering to the subject an effective amount of a dengue virus epitope, a polypeptide, a chimeric flavivirus VLP or chimeric flavivirus particle, nucleic acid, vector, cell, or immunogenic composition of the invention.

A still further aspect of the invention is a method of preventing a dengue virus infection, comprising administering to the subject an effective amount of a dengue virus epitope, a polypeptide, a chimeric flavivirus VLP or chimeric flavivirus particle, nucleic acid, vector, cell, or immunogenic composition of the invention.

A still further aspect of the invention is a method of protecting a subject from the effects of dengue virus infection, comprising administering to the subject an effective amount of a dengue virus epitope, a polypeptide, a chimeric flavivirus VLP or chimeric flavivirus particle, nucleic acid, vector, cell, or immunogenic composition of the invention.

There are four serotypes of dengue virus (DENV-1, DENV-2, DENV-3 and DENV-4). Within each serotype there are a number of different strains or genotypes. The dengue virus antigens and epitopes of the invention can be derived from any dengue virus, including all serotypes, strains and genotypes, now known or later identified.

In embodiments of the invention, the dengue virus is UNC1017 strain (DEN1), West Pacific 74 strain (DEN1), S16803 strain (DEN2), UNC2005 strain (DEN2), UNC3001 strain (DEN3), UNC3043 (DEN3 strain 059.AP-2 from Philippines, 1984), UNC3009 strain (DEN3, D2863, Sri Lanka 1989), UNC3066 (DEN3, strain 1342 from Puerto Rico 1977), CH53489 strain (DEN3), UNC4019 strain (DEN4), or TVP-360 (DEN4).

In embodiments of the invention, an "immunogenically active fragment" of a dengue virus polypeptide (e.g., the E protein) comprises, consists essentially of or consists of at least about 6, 8, 10, 12, 15, 20, 30, 50, 75, 100, 125, 150, 200, 250, 300, 350, 400, 450 or more amino acids, optionally contiguous amino acids, and/or less than about 495, 475, 450, 425, 400, 350, 300, 250, 200, 150, 100, 75 or 50 amino acids, optionally contiguous amino acids, including any combination of the foregoing as long as the lower limit is less than the upper limit, and the "immunogenically active fragment" induces an immune response (e.g., IgG and/or IgA that react with the native antigen), optionally a protective immune response, against dengue virus in a host and induces the production of antibodies that specifically bind to the quaternary dengue virus epitope newly identified by the inventors.

The term "epitope" as used herein means a specific amino acid sequence that, when present in the proper conformation, provides a reactive site for an antibody (e.g., B cell epitope) or T cell receptor (e.g., T cell epitope).

Portions of a given polypeptide that include a B-cell epitope can be identified using any number of epitope mapping techniques that are known in the art. (See, e.g., *Epitope Mapping Protocols in Methods in Molecular Biology*, Vol. 66, Glenn E. Morris, Ed., 1996, Humana Press, Totowa, N.J.). For example, linear epitopes can be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad Sci. USA* 81:3998-4002; Geysen et al. (1986) *Molec. Immunol.* 23:709-715.

Similarly, conformational epitopes can be readily identified by determining spatial conformation of amino acids such as by, e.g., x-ray crystallography and 2-dimensional nuclear magnetic resonance. Antigenic regions of proteins can also be identified using standard antigenicity and hydropathy plots, such as those calculated using, e.g., the Omiga version 1.0 software program available from the Oxford Molecular Group. This computer program employs the Hopp/Woods method (Hopp et al., *Proc. Natl. Acad Sci USA* (1981) 78:3824-3828) for determining antigenicity profiles and the Kyte-Doolittle technique (Kyte et al., *J. Mol. Biol.* (1982) 157:105-132) for hydropathy plots.

Generally, T-cell epitopes that are involved in stimulating the cellular arm of a subject's immune system are short peptides of about 8-25 amino acids. A common way to identify T-cell epitopes is to use overlapping synthetic peptides and analyze pools of these peptides, or the individual ones, that are recognized by T cells from animals that are immune to the antigen of interest, using, for example, an enzyme-linked immunospot assay (ELISPOT). These overlapping peptides can also be used in other assays such as the stimulation of cytokine release or secretion, or evaluated by constructing major histocompatibility (MHC) tetramers containing the peptide. Such immunogenically active fragments can also be identified based on their ability to stimulate lymphocyte proliferation in response to stimulation by various fragments from the antigen of interest.

The present invention can be practiced for prophylactic, therapeutic and/or diagnostic purposes. In addition, the invention can be practiced to produce antibodies for any purpose, such as diagnostic or research purposes, or for passive immunization by transfer to another subject.

The present invention further provides a kit comprising one or more compositions of this invention. It would be well understood by one of ordinary skill in the art that the kit of this invention can comprise one or more containers and/or receptacles to hold the reagents (e.g., antibodies, antigens, nucleic acids) of the kit, along with appropriate buffers and/or diluents and/or other solutions and directions for using the kit, as would be well known in the art. Such kits can further comprise adjuvants and/or other immunostimulatory or immunomodulating agents, as are well known in the art.

The compositions and kits of the present invention can also include other medicinal agents, pharmaceutical agents, carriers, diluents, immunostimulatory cytokines, etc. Actual methods of preparing such dosage forms are known, or will be apparent, to those skilled in this art.

Administration to a subject can be by any route known in the art. As non-limiting examples, the route of administration can be by inhalation (e.g., oral and/or nasal inhalation), oral, buccal (e.g., sublingual), rectal, vaginal, topical (including administration to the airways), intraocular, transdermal, by parenteral (e.g., intramuscular [e.g., administration to skeletal muscle], intravenous, intra-arterial, intraperitoneal and the like), subcutaneous (including administration into the footpad), intradermal, intrapleural, intracerebral, and/or intrathecal routes.

The epitopes, polypeptides, VLPs and viral vectors of the invention can be delivered per se or by delivering a nucleic acid (e.g., DNA) that encodes the same.

Immunomodulatory compounds, such as immunomodulatory chemokines and cytokines (preferably, CTL inductive cytokines) can be administered concurrently to a subject.

Cytokines may be administered by any method known in the art. Exogenous cytokines may be administered to the subject, or alternatively, a nucleic acid encoding a cytokine may be delivered to the subject using a suitable vector, and the cytokine produced in vivo. In particular embodiments, a viral adjuvant expresses the cytokine.

In embodiments of the invention, multiple dosages (e.g., two, three or more) of a composition of the invention can be administered without detectable pathogenicity (e.g., Dengue Shock Syndrome/Dengue Hemorrhagic Fever).

In embodiments of the invention, the multivalent vaccines of the invention do not result in immune interference, e.g., a balanced immune response is induced against all antigens presented. In embodiments of the invention, the balanced response results in protective immunity against DENV-1, DENV-2, DENV-3 and DENV-4.

In embodiments of the invention, the multivalent vaccine can be administered to a subject that has anti-dengue maternal antibodies present.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a fatty acid) and the like, is meant to encompass variations of ±20% Y, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 U.S.P.Q. 461,463 (CCPA 1976) (emphasis in the original); see also MPEP § 2111.03. Thus, the term "consisting essentially of" when used in a claim of this invention is not intended to be interpreted to be equivalent to "comprising."

As used herein, the term "nucleic acid" encompasses both RNA and DNA, including cDNA, genomic DNA, synthetic (e.g., chemically synthesized) DNA and chimeras of RNA and DNA. The nucleic acid may be double-stranded or single-stranded. The nucleic acid may be synthesized using nucleotide analogs or derivatives (e.g., inosine or phosphorothioate nucleotides). Such nucleotides can be used, for example, to prepare nucleic acids that have altered base-pairing abilities or increased resistance to nucleases.

As used herein, the term "polypeptide" encompasses both peptides and proteins (including fusion proteins), unless indicated otherwise.

A "fusion protein" is a polypeptide produced when two heterologous nucleotide sequences or fragments thereof coding for two (or more) different polypeptides not found fused together in nature are fused together in the correct translational reading frame.

A "recombinant" nucleic acid, polynucleotide or nucleotide sequence is one produced by genetic engineering techniques.

A "recombinant" polypeptide is produced from a recombinant nucleic acid, polypeptide or nucleotide sequence.

As used herein, an "isolated" polynucleotide (e.g., an "isolated nucleic acid" or an "isolated nucleotide sequence") means a polynucleotide at least partially separated from at least some of the other components of the naturally occurring organism or virus, for example, the cell or viral structural components or other polypeptides or nucleic acids commonly found associated with the polynucleotide. Optionally, but not necessarily, the "isolated" polynucleotide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polynucleotide is at least about 1%, 5%, 10%, 20%, 30%, 40%, 50%, 60%, 70%, 80%, 90%, 95% or more pure.

An "isolated" polypeptide means a polypeptide that is at least partially separated from at least some of the other components of the naturally occurring organism or virus, for example, the cell or viral structural components or other polypeptides or nucleic acids commonly found associated with the polypeptide. Optionally, but not necessarily, the "isolated" polypeptide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polypeptide is at least about 1%, 5%, 10%, 20%, 30%, 40%, 50%, 60%, 70%, 80%, 90%, 95% or more pure.

Furthermore, an "isolated" cell is a cell that has been partially or completely separated from other components with which it is normally associated in nature. For example, an isolated cell can be a cell in culture medium and/or a cell in a pharmaceutically acceptable carrier.

The terms "immunogen" and "antigen" are used interchangeably herein and mean any compound (including polypeptides) to which a cellular and/or humoral immune response can be directed. In particular embodiments, an immunogen or antigen can induce a protective immune response against the effects of dengue virus infection.

"Effective amount" as used herein refers to an amount of a vector, nucleic acid, epitope, polypeptide, cell, particle, VLP, composition or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation.

The term "immunogenic amount" or "effective immunizing dose," as used herein, unless otherwise indicated, means an amount or dose sufficient to induce an immune response (which can optionally be a protective response) in the treated subject that is greater than the inherent immunity of non-immunized subjects. An immunogenic amount or effective immunizing dose in any particular context can be routinely determined using methods known in the art.

The terms "vaccine," "vaccination" and "immunization" are well-understood in the art, and are used interchangeably herein. For example, the terms vaccine, vaccination or immunization can be understood to be a process or composition that increases a subject's immune reaction to an immunogen (e.g., by providing an active immune response), and therefore its ability to resist, overcome and/or recover from infection (i.e., a protective immune response).

By the terms "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. In representative embodiments, the terms "treat," "treating" or "treatment of" (and grammatical variations thereof) refer to a reduction in the severity of viremia and/or a delay in the progression of viremia, with or without other signs of clinical disease.

A "treatment effective" amount as used herein is an amount that is sufficient to treat (as defined herein) the subject. Those skilled in the art will appreciate that the therapeutic effects need not be complete or curative, as long as some benefit is provided to the subject.

The term "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the terms "prevent," "preventing" or "prevention of" (and grammatical variations thereof) refer to prevention and/or delay of the onset and/or progression of viremia in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The efficacy of treating and/or preventing dengue virus infection by the methods of the present invention can be determined by detecting a clinical improvement as indicated by a change in the subject's symptoms and/or clinical parameters (e.g., viremia), as would be well known to one of skill in the art.

Unless indicated otherwise, the terms "protect," "protecting," "protection" and "protective" (and grammatical variations thereof) encompass both methods of preventing and treating dengue virus infection in a subject, whether against one or multiple strains, genotypes or serotypes of dengue virus.

The terms "protective" immune response or "protective" immunity as used herein indicates that the immune response confers some benefit to the subject in that it prevents or reduces the incidence and/or severity and/or duration of disease or any other manifestation of infection. For example, in representative embodiments, a protective immune response or protective immunity results in reduced viremia, whether or not accompanied by clinical disease. Alternatively, a protective immune response or protective immunity may be useful in the therapeutic treatment of existing disease.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "subject" of the invention includes any animal susceptible to dengue virus infection. Such a subject is generally a mammalian subject (e.g., a laboratory animal such as a rat, mouse, guinea pig, rabbit, primates, etc.), a farm or commercial animal (e.g., a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. Subjects of the invention can be a subject known or believed to be at risk of infection by dengue virus. Alternatively, a subject according to the invention can also include a subject not previously known or suspected to be infected by dengue virus or in need of treatment for dengue virus infection.

Subjects may be treated for any purpose, such as for eliciting a protective immune response or for eliciting the production of antibodies in that subject, which antibodies can be collected and used for other purposes such as research or diagnostic purposes or for administering to other subjects to produce passive immunity therein, etc.

Subjects include males and/or females of any age, including neonates, juvenile, mature and geriatric subjects. With respect to human subjects, in representative embodiments, the subject can be an infant (e.g., less than about 12 months, 10 months, 9 months, 8 months, 7 months, 6 months, or younger), a toddler (e.g., at least about 12, 18 or 24 months and/or less than about 36, 30 or 24 months), or a child (e.g., at least about 1, 2, 3, 4 or 5 years of age and/or less than about 14, 12, 10, 8, 7, 6, 5, or 4 years of age). In embodiments of the invention, the subject is a human subject that is from about 0 to 3, 4, 5, 6, 9, 12, 15, 18, 24, 30, 36, 48 or 60 months of age, from about 3 to 6, 9, 12, 15, 18, 24, 30, 36, 48 or 60 months of age, from about 6 to 9, 12, 15, 18, 24, 30, 36, 48 or 60 months of age, from about 9 to 12, 15, 18, 24, 30, 36, 48 or 60 months of age, from about 12 to 18, 24, 36, 48 or 60 months of age, from about 18 to 24, 30, 36, 48 or 60 months of age, or from about 24 to 30, 36, 48 or 60 months of age.

In embodiments of the invention, the subject has maternal antibodies to dengue virus.

A "subject in need" of the methods of the invention can be a subject known to be, or suspected of being, infected with, or at risk of being infected with, dengue virus.

Pharmaceutical formulations (e.g., immunogenic formulation) comprising the dengue virus epitopes, polypeptides, chimeric flavivirus VLPs or chimeric flavivirus particles, nucleic acids, vectors, cells or compositions of the invention and a pharmaceutically acceptable carrier are also provided, and can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of the invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of the invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

In some embodiments, the compositions of the invention can further comprise one or more than one adjuvant. The adjuvants of the present invention can be in the form of an amino acid sequence, and/or in the form or a nucleic acid encoding an adjuvant. When in the form of a nucleic acid, the adjuvant can be a component of a nucleic acid encoding the polypeptide(s) or fragment(s) or epitope(s) and/or a separate component of the composition comprising the nucleic acid encoding the polypeptide(s) or fragment(s) or epitope(s) of the invention. According to the present invention, the adjuvant can also be an amino acid sequence that is a peptide, a protein fragment or a whole protein that functions as an adjuvant, and/or the adjuvant can be a nucleic acid encoding a peptide, protein fragment or whole protein that functions as an adjuvant. As used herein, "adjuvant" describes a substance, which can be any immunomodulating substance capable of being combined with a composition of the invention to enhance, improve or otherwise modulate an immune response in a subject.

In further embodiments, the adjuvant can be, but is not limited to, an immunostimulatory cytokine (including, but not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules), SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, or may be an insoluble suspension of acylated tyrosine, or acylated sugars, cationically or anionically derivatized polysaccharides, or polyphosphazenes.

Other adjuvants are well known in the art and include without limitation MF 59, LT-K63, LT-R72 (Pal et al., Vaccine 24(6):766-75 (2005)), QS-21, Freund's adjuvant (complete and incomplete), aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

Additional adjuvants can include, for example, a combination of monophosphoryl lipid A, preferably 3-de-O-acylated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153, or a less reactogenic composition where the QS21 is quenched with cholesterol as disclosed in PCT publication number WO 96/33739. A particularly potent adjuvant formulation involving QS21 3D-MPL & tocopherol in an oil in water emulsion is described in PCT publication number WO 95/17210. In addition, the nucleic acid compositions of the invention can include an adjuvant by comprising a nucleotide sequence encoding the antigen and a nucleotide sequence that provides an adjuvant function, such as CpG sequences. Such CpG sequences, or motifs, are well known in the art.

An adjuvant for use with the present invention, such as, for example, an immunostimulatory cytokine, can be administered before, concurrent with, and/or within a few hours, several hours, and/or 1, 2, 3, 4, 5, 6, 7, 8, 9, and/or 10 days before and/or after the administration of a composition of the invention to a subject.

Furthermore, any combination of adjuvants, such as immunostimulatory cytokines, can be co-administered to the subject before, after and/or concurrent with the administration of an immunogenic composition of the invention. For example, combinations of immunostimulatory cytokines, can consist of two or more immunostimulatory cytokines, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants can be determined by measuring the immune response produced in response to administration of a composition of this invention to a subject with and without the adjuvant or combination of adjuvants, using standard procedures, as described herein and as known in the art.

In embodiments of the invention, the adjuvant comprises an alphavirus adjuvant as described, for example in U.S. Pat. No. 7,862,829.

Boosting dosages can further be administered over a time course of days, weeks, months or years. In chronic infection, initial high doses followed by boosting doses may be advantageous.

The pharmaceutical formulations of the invention can optionally comprise other medicinal agents, pharmaceutical agents, stabilizing agents, buffers, carriers, diluents, salts, tonicity adjusting agents, wetting agents, and the like, for example, sodium acetate, sodium lactate, sodium chloride, potassium chloride, calcium chloride, sorbitan monolaurate, triethanolamine oleate, etc.

For injection, the carrier will typically be a liquid. For other methods of administration, the carrier may be either solid or liquid. For inhalation administration, the carrier will be respirable, and is typically in a solid or liquid particulate form.

The compositions of the invention can be formulated for administration in a pharmaceutical carrier in accordance with known techniques. See, e.g., Remington, The Science And Practice of Pharmacy ($9^{th}$ Ed. 1995). In the manufacture of a pharmaceutical composition according to the invention, the VLPs are typically admixed with, inter alia, an acceptable carrier. The carrier can be a solid or a liquid, or both, and is optionally formulated with the compound as a unit-dose formulation, for example, a tablet. A variety of pharmaceutically acceptable aqueous carriers can be used, e.g., water, buffered water, 0.9% saline, 0.3% glycine, hyaluronic acid, pyrogen-free water, pyrogen-free phosphate-buffered saline solution, bacteriostatic water, or Cremophor EL[R] (BASF, Parsippany, N.J.), and the like. These compositions can be sterilized by conventional techniques. The formulations of the invention can be prepared by any of the well-known techniques of pharmacy.

The pharmaceutical formulations can be packaged for use as is, or lyophilized, the lyophilized preparation generally being combined with a sterile aqueous solution prior to administration. The compositions can further be packaged in unit/dose or multi-dose containers, for example, in sealed ampoules and vials.

The pharmaceutical formulations can be formulated for administration by any method known in the art according to conventional techniques of pharmacy. For example, the compositions can be formulated to be administered intranasally, by inhalation (e.g., oral inhalation), orally, buccally (e.g., sublingually), rectally, vaginally, topically, intrathecally, intraocularly, transdermally, by parenteral administration (e.g., intramuscular [e.g., skeletal muscle], intravenous, subcutaneous, intradermal, intrapleural, intracerebral and intra-arterial, intrathecal), or topically (e.g., to both skin and mucosal surfaces, including airway surfaces).

For intranasal or inhalation administration, the pharmaceutical formulation can be formulated as an aerosol (this term including both liquid and dry powder aerosols). For example, the pharmaceutical formulation can be provided in a finely divided form along with a surfactant and propellant. Typical percentages of the composition are 0.01-20% by weight, preferably 1-10%. The surfactant is generally non-toxic and soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1-20% by weight of the composition, preferably 0.25-5%. The balance of the composition is ordinarily propellant. A carrier can also be included, if desired, as with lecithin for intranasal delivery. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles can likewise be produced with any solid particulate medicament aerosol generator, by techniques known in the pharmaceutical art. Intranasal administration can also be by droplet administration to a nasal surface.

Injectable formulations can be prepared in conventional forms, either as liquid solutions or suspensions, solid forms suitable for solution or suspension in liquid prior to injection, or as emulsions. Alternatively, one can administer the pharmaceutical formulations in a local rather than systemic manner, for example, in a depot or sustained-release formulation.

Extemporaneous injection solutions and suspensions can be prepared from sterile powders, granules and tablets of the kind previously described. For example, an injectable, stable, sterile formulation of the invention in a unit dosage form in a sealed container can be provided. The formulation can be provided in the form of a lyophilizate, which can be reconstituted with a suitable pharmaceutically acceptable carrier to form a liquid composition suitable for injection into a subject. The unit dosage form can be from about 1 μg to about 10 grams of the formulation. When the formulation is substantially water-insoluble, a sufficient amount of emulsifying agent, which is pharmaceutically acceptable, can be included in sufficient quantity to emulsify the formulation in an aqueous carrier. One such useful emulsifying agent is phosphatidyl choline.

Pharmaceutical formulations suitable for oral administration can be presented in discrete units, such as capsules, cachets, lozenges, or tables, as a powder or granules; as a solution or a suspension in an aqueous or non-aqueous liquid; or as an oil-in-water or water-in-oil emulsion. Oral delivery can be performed by complexing a compound(s) of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the protein(s) and a suitable carrier (which may contain one or more accessory ingredients as noted above). In general, the pharmaceutical formulations are prepared by uniformly and intimately admixing the compound(s) with a liquid or finely divided solid carrier, or both, and then, if necessary, shaping the resulting mixture. For example, a tablet can be prepared by compressing or molding a powder or granules, optionally with one or more accessory ingredients. Compressed tablets are prepared by compressing, in a suitable machine, the formulation in a free-flowing form, such as a powder or granules optionally mixed with a binder, lubricant, inert diluent, and/or surface active/dispersing agent(s). Molded tablets are made by molding, in a suitable machine, the powdered protein moistened with an inert liquid binder.

Pharmaceutical formulations suitable for buccal (sub-lingual) administration include lozenges comprising the compound(s) in a flavored base, usually sucrose and acacia or tragacanth; and pastilles in an inert base such as gelatin and glycerin or sucrose and acacia.

Pharmaceutical formulations suitable for parenteral administration can comprise sterile aqueous and non-aqueous injection solutions, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations suitable for rectal administration are optionally presented as unit dose suppositories. These can be prepared by admixing the active agent with one or more conventional solid carriers, such as for example, cocoa butter and then shaping the resulting mixture.

Pharmaceutical formulations suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical formulation of the present invention with a lipophilic reagent (e.g., DMSO) that is capable of passing into the skin.

Pharmaceutical formulations suitable for transdermal administration can be in the form of discrete patches adapted to remain in intimate contact with the epidermis of the subject for a prolonged period of time. Formulations suitable for transdermal administration can also be delivered by iontophoresis (see, for example, Pharmaceutical Research 3:318 (1986)) and typically take the form of a buffered aqueous solution of the compound(s). Suitable formulations can comprise citrate or bis\tris buffer (pH 6) or ethanol/water and can contain from 0.1 to 0.2M active ingredient.

In embodiments of the invention, the dosage of a virus particle of this invention can be in a range of about $10^4$ to about $10^7$ plaque forming units (PFUs). In embodiments of this invention, the dosage of a VLP of this invention can be in a range of about 500 micrograms to about 5 milligrams. In embodiments of this invention, the dosage of a protein of this invention can be in a range of about $10^0$ to about $10^4$ micrograms+/−adjuvant.

Further, the composition can be formulated as a liposomal formulation. The lipid layer employed can be of any conventional composition and can either contain cholesterol or can be cholesterol-free. The liposomes that are produced can be reduced in size, for example, through the use of standard sonication and homogenization techniques.

The liposomal formulations can be lyophilized to produce a lyophilizate which can be reconstituted with a pharmaceutically acceptable carrier, such as water, to regenerate a liposomal suspension.

The immunogenic formulations of the invention can optionally be sterile, and can further be provided in a closed pathogen-impermeable container.

EXAMPLES

Synthetic biology offers unparalleled genetic control over the genome structure, expression and organization of viral genomes. The dengue virus (DENV) complex consists of four closely related viruses designated DENV serotypes 1-4, which are antigenically similar yet induce complex patterns of cross reactive neutralizing and enhancing antibody responses in human populations. To study the antigenic relationships among the DENV serotypes, we describe the construction and characterization of a panel of stable DENV1-4 molecular clones and recombinant viruses based on a low passage clinical isolates. Recombinant viruses replicated like wildtype viruses and encoded appropriate marker mutations. To evaluate the role of natural variation in DENV3, four synthetically designed isogenic constructs were made by replacing the parent envelope (E) glycoprotein gene with E genes based on the four genetically and geographically distinct DENV-3 genotypes. Recombinant viruses were viable, evaluated for growth on insect and mammalian hosts, and monoclonal and polyclonal neutralization tests demonstrate that natural microvariation among DEN3 neutralization influences cross neutralization susceptibility patterns. To evaluate the use of recombinant DNA technology to map defined epitopes, we used escape mutations and epitope mapping to map the coordinates of several epitopes. Then, we exchanged these epitopes between strains. Recombinant viruses were viable and gain and loss of function assays with monoclonal and polyclonal sera revealed antigenic patterns that reveal important considerations in vaccine design.

The anti-dengue virus (DENV) human monoclonal antibody (mAb) 5J7 potently neutralizes DENV serotype 3 (DENV-3) by binding to an epitope on the DENV-3 envelope (E) glycoprotein. This epitope spans the E region known as the E domain I-II (EDI-II) hinge. Using a DENV infection clone platform, the DENV-3 5J7 epitope was transplanted into a DENV serotype 1 (DENV-1) E glycoprotein. This transplant makes the recombinant DENV-1/3 virus sensitive to neutralization by mAb 5J7. Significantly, the transplant does not disrupt the native DENV-1 antigenic structure, and the recombinant virus is sensitive to both DENV-1 and DENV-3 human polyclonal sera. This sensitivity indicates that the DENV-1/3 chimeric E glycoprotein may function as a bivalent vaccine capable of inducing neutralizing antibodies against two virus serotypes—DENV-1 and DENV-3.

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

TABLE 1

Amino acid substitutions to produce DENV-1/3 and DENV-3/1

| EAA# | 50 | 52 | 53 | 55 | 125 | 129 | 161 | 197 | 202 | 203 | 205 | 207 | 210 | 272 | 275 | 277 | | | | | |
|---|---|---|---|---|---|---|---|---|---|---|---|---|---|---|---|---|---|---|---|---|---|
| WestPac'74 | V | N | P | V | L | I | T | V | E | K | W | L | K | T | T | T | | | | | |
| DENV-1/3 hinge | A | Q | L | T | I | V | I | I | K | N | A | M | R | N | G | S | | | | | |

| EAA# | 46 | 50 | 52 | 53 | 138 | 141 | 155 | 156 | 157 | 160 | 163 | 169 | 171 | 173 | 174 | 176 | 177 | 180 | 272 | 275 | 277 |
|---|---|---|---|---|---|---|---|---|---|---|---|---|---|---|---|---|---|---|---|---|---|
| 3001 | Q | A | Q | L | T | I | T | - | - | V | E | S | T | A | I | P | E | T | N | G | S |
| Denv-3/1 | L | V | N | P | S | V | V | T | E | T | T | P | S | I | Q | T | D | A | T | T | T |

TABLE 2

Nucleotide substitutions in WestPac'74 (DENV-1) CDS to produce DENV 1-3 hinge

| nt. Position | 1083 | 1087 | 1088 | 1090 | 1092 | 1093 | 1096 | 1097 | 1098 | 1102 |
|---|---|---|---|---|---|---|---|---|---|---|
| WestPac'74 | T | A | A | C | C | T | C | G | T | G |
| DENV-1/3hinge | C | C | C | A | T | G | G | A | C | A |

TABLE 2-continued

Nucleotide substitutions in WestPac'74 (DENV-1) CDS to produce DENV 1-3 hinge

| nt. Position | 1103 | 1105 | 1108 | 1111 | 1307 | 1309 | 1311 | 1318 | 1319 | 1321 |
|---|---|---|---|---|---|---|---|---|---|---|
| WestPac'74 | C | C | A | G | C | G | A | G | A | A |
| DENV-1/3 hinge | A | G | G | A | A | A | G | A | G | G |

| nt. Position | 1324 | 1416 | 1510 | 1513 | 1519 | 1523 | 1525 | 2528 | 2529 | 1531 |
|---|---|---|---|---|---|---|---|---|---|---|
| WestPac'74 | C | C | C | T | G | G | G | G | T | G |
| DENV-1/3 hinge | G | T | T | C | A | A | C | A | C | A |

| nt. Position | 1538 | 1543 | 1547 | 1553 | 1555 | 1558 | 1561 | 1563 | 1724 | 1729 |
|---|---|---|---|---|---|---|---|---|---|---|
| WestPac'74 | G | A | T | C | C | C | C | A | T | T |
| DENV-1/3 hinge | A | C | G | A | G | A | T | G | C | A |

| nt. Position | 1735 | 1749 | 1750 | 1753 | 1757 | 1758 | 1759 | 1764 | 1765 | 1774 |
|---|---|---|---|---|---|---|---|---|---|---|
| WestPac'74 | G | C | G | T | A | C | G | C | A | A |
| DENV-1/3 hinge | C | A | C | A | G | G | C | G | C | G |

TABLE 3

Viremia (Log FFU/mL)

| RM I.D. | Challenge Virus | Day 1 | Day 2 | Day 3 | Day 4 | Day 5 | Day 6 | Day 7 | Day 8 | Day 9 | Day 10 | Days viremia |
|---|---|---|---|---|---|---|---|---|---|---|---|---|
| BM05 |  | — | 2.0 | — | 2.1 | 1.7 | 2.4 | — | 1.4 | — | — | 5 |
| BP34 | rDENV1/3 | — | — | 1.7 | — | 2.1 | 2.4 | 1.9 | — | — | — | 4 |
| BP73 |  | — | 1.7 | — | 2.0 | 1.9 | 2.6 | 1.4 | — | — | — | 5 |
| BS69 |  | — | 2.3 | 1.9 | 2.0 | 2.4 | — | 2.1 | — | — | — | 5 |

TABLE 4

Viremia (Log FFU/mL)

| RM I.D. | Challenge Virus | Day 1 | Day 2 | Day 3 | Day 4 | Day 5 | Day 6 | Day 7 | Day 8 | Day 9 | Day 10 | Days viremia |
|---|---|---|---|---|---|---|---|---|---|---|---|---|
| OL3 |  | − | − | − | + | + | + | + | − | − | − | 4 |
| 3J6 | 3001-F4E | − | + | − | + | + | − | − | − | − | − | 3 |
| 8K2 |  | − | − | − | − | + | − | − | − | − | − | 1 |
| 7L2 |  | − | − | − | + | − | − | − | − | − | − | 1 |

TABLE 5

| Mabs | Donor | Virus Binding | Protein binding | | Neut50 (µg/ml) | | | |
|---|---|---|---|---|---|---|---|---|
| | | | rE | ED III | DV1 | DV2 | DV3 | DV4 |
| 1B19 | HD184 | Complex | + | − | 1.2 | 1.8 | 2.9 | 5.7 |
| 1B22 | HD184 | Complex | − | − | >10 | >10 | >10 | >10 |
| 1B23 | 19 | Complex | + | + | 7.7 | 9.77 | 3.1 | 18.6 |
| 1C6 | Harris Acute | Complex | − | − | >10 | >10 | 1.55 | >10 |
| 10000 | HD184 | Complex | + | + | 1.1 | 1 | 3.4 | 4 |
| 1F4 | HD184 | DENV-1 | − | − | 0.11 | >10 | >10 | >10 |
| 1F16.2 | Harris Acute | Complex | + | + | 3.93 | 5 | 12 | 20.9 |
| 1G10 | Harris Acute | Complex | + | − | >10 | >10 | 0.093 | >10 |
| 1H10 | HD184 | Complex | − | − | >10 | >10 | 0.37 | 4.3 |
| 1H16 | Harris Acute | Complex | − | − | >10 | >10 | >10 | >10 |
| 1I12 | HD184 | Complex | − | − | >10 | >10 | 0.36 | >10 |
| 1L6 | HD184 | Complex | + | − | 2.34 | 6.7 | 1.1 | 6.25 |
| 1L13 | Vaccine | Complex | − | − | >10 | >10 | 0.24 | >10 |
| 1M19 | 19 | Complex | + | − | 4.6 | 6.7 | 0.28 | 5.9 |
| 1N5 | Harris Acute | Complex | + | − | 0.27 | .04 | 0.98 | 0.85 |
| 1N8 | HD184 | Complex | + | − | 4.5 | 4.1 | 7.65 | 5.95 |
| 2M11 | HD184 | Complex | + | − | 1.72 | 2.62 | 3.61 | 4.36 |
| 3B4 | HD184 | Complex | + | − | 1.77 | 2.23 | 1.26 | 1.61 |
| 5C8 | HD184 | Complex | + | − | 1.07 | 1.65 | 0.95 | 3.31 |

TABLE 5-continued

| Mabs | Donor | Virus Binding | Protein binding | | Neut50 (μg/ml) | | | |
|---|---|---|---|---|---|---|---|---|
| | | | rE | ED III | DV1 | DV2 | DV3 | DV4 |
| 5J7 | 105 | Complex | − | − | >10 | >10 | 0.09 | >10 |
| 5K17 | HD184 | Complex | + | − | 2.28 | 3.16 | 6.21 | 4.71 |

That which is claimed is:

1. A chimeric dengue virus E glycoprotein comprising a dengue virus E glycoprotein backbone that comprises the following amino acid substitutions that introduce an epitope that is recognized by an antibody that is reactive with a dengue virus serotype that is different from the dengue virus serotype of the dengue virus E glycoprotein backbone; wherein the amino acid residue numbering is based on the reference amino acid sequence of an E glycoprotein of dengue virus serotype 3 (DENV3) identified as SEQ ID NO:1: T138S, Q158H, V160T, S169P, A173I, I174Q, P176T, E177D, N272T, G275T, and S277T, and wherein said dengue virus E glycoprotein further comprises an insertion of the amino acid residues T and E between amino acid residues 155 and 156.

2. A flavivirus particle or virus like particle (VLP) comprising the chimeric dengue virus E glycoprotein of claim 1.

3. A composition comprising the chimeric dengue virus E glycoprotein of claim 1 in a pharmaceutically acceptable carrier.

4. A composition comprising the flavivirus particle or VLP of claim 2 in a pharmaceutically acceptable carrier.

5. A method of producing an immune response to a dengue virus in a subject, comprising administering to the subject an effective amount of the chimeric dengue virus E glycoprotein of claim 1.

6. A method of producing an immune response to a dengue virus in a subject, comprising administering to the subject an effective amount of the flavivirus particle or VLP of claim 2.

* * * * *

UNITED STATES PATENT AND TRADEMARK OFFICE
CERTIFICATE OF CORRECTION

PATENT NO. : 10,870,682 B2
APPLICATION NO. : 16/105346
DATED : December 22, 2020
INVENTOR(S) : Messer et al.

Page 1 of 1

It is certified that error appears in the above-identified patent and that said Letters Patent is hereby corrected as shown below:

In the Specification

Column 11, Line 14: Please correct "±20% Y, ±10%," to read -- ±20%, ±10%, --

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 6

<210> SEQ ID NO 1
<211> LENGTH: 393
<212> TYPE: PRT
<213> ORGANISM: Dengue virus type 3

<400> SEQUENCE: 1

```
Met Arg Cys Val Gly Ile Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Pro Ile Glu Gly Lys
        115                 120                 125

Val Val Gln Tyr Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Ile Ile Thr Pro Gln Ala Ser Thr Thr Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Glu Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Asn Ser Gly
            260                 265                 270

Gly Thr Ser Ile Phe Ala Gly His Leu Lys Cys Arg Leu Lys Met Asp
        275                 280                 285

Lys Leu Glu Leu Lys Gly Met Ser Tyr Ala Met Cys Thr Asn Thr Phe
    290                 295                 300
```

```
Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
        355                 360                 365

Pro Pro Phe Gly Glu Ser Asn Ile Val Ile Gly Ile Gly Asp Asn Ala
    370                 375                 380

Leu Lys Ile Asn Trp Tyr Lys Lys Gly
385                 390
```

<210> SEQ ID NO 2
<211> LENGTH: 395
<212> TYPE: PRT
<213> ORGANISM: Dengue virus type 1

<400> SEQUENCE: 2

```
Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Glu Lys Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285
```

```
Met Asp Lys Leu Thr Leu Lys Gly Met Ser Tyr Val Met Cys Thr Gly
        290                 295                 300
Ser Phe Lys Leu Glu Lys Glu Val Ala Glu Thr Gln His Gly Thr Val
305                 310                 315                 320
Leu Val Gln Val Lys Tyr Glu Gly Thr Asp Ala Pro Cys Lys Ile Pro
                    325                 330                 335
Phe Ser Ser Gln Asp Glu Lys Gly Val Thr Gln Asn Gly Arg Leu Ile
                340                 345                 350
Thr Ala Asn Pro Ile Val Thr Asp Lys Glu Lys Pro Val Asn Ile Glu
            355                 360                 365
Ala Glu Pro Pro Phe Gly Glu Ser Tyr Ile Val Val Gly Ala Gly Glu
        370                 375                 380
Lys Ala Leu Lys Leu Ser Trp Phe Lys Lys Gly
385                 390                 395

<210> SEQ ID NO 3
<211> LENGTH: 395
<212> TYPE: PRT
<213> ORGANISM: Artificial
<220> FEATURE:
<223> OTHER INFORMATION: WestPac74 hinge (DENV 1/3)

<400> SEQUENCE: 3

Met Arg Cys Val Gly Ile Gly Asn Arg Asp Phe Val Glu Gly Leu Ser
1               5                   10                  15
Gly Ala Thr Trp Val Asp Val Val Leu Glu His Gly Ser C

```
Glu Gly Ala Met His Thr Ala Leu Thr Gly Ala Thr Glu Ile Gln Asn
                260                 265                 270

Ser Gly Gly Thr Ser Ile Phe Ala Gly His Leu Lys Cys Arg Leu Lys
            275                 280                 285

Met Asp Lys Leu Thr Leu Lys Gly Met Ser Tyr Val Met Cys Thr Gly
290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
                340                 345                 350

Thr Ala Asn Pro Ile Val Thr Asp Lys Glu Lys Pro Val Asn Ile Glu
            355                 360                 365

Ala Glu Pro Pro Phe Gly Glu Ser Tyr Ile Val Val Gly Ala Gly Glu
        370                 375                 380

Lys Ala Leu Lys Leu Ser Trp Phe Lys Lys Gly
385                 390                 395

<210> SEQ ID NO 4
<211> LENGTH: 395
<212> TYPE: PRT
<213> ORGANISM: Artificial
<220> FEATURE:
<223> OTHER INFORMATION: 3001-1F4E (DENV 3/1)

<400> SEQUENCE: 4

Met Arg Cys Val Gly Ile Gly Asn Arg Asp Phe Val Glu Gly Leu Ser
1               5                   10                  15

Gly Ala Thr Trp Val Asp Val Val Leu Glu His Gly Gly Cys Val Th

Thr Thr Glu Thr Pro Thr Trp Asn Arg Lys Glu Leu Leu Val Thr Phe
225                 230                 235                 240

Lys Asn Ala His Ala Lys Lys Gln Glu Val Val Leu Gly Ser Gln
            245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Glu Leu Lys Gly Met Ser Tyr Ala Met Cys Thr Asn
        290                 295                 300

Thr Phe Val Leu Lys Lys Glu Val Ser Glu Thr Gln His Gly Thr Ile
305                 310                 315                 320

Leu Ile Lys Val Glu Tyr Lys Gly Glu Asp Ala Pro Cys Lys Ile Pro
                325                 330                 335

Phe Ser Thr Glu Asp Gly Gln Gly Lys Ala His Asn Gly Arg Leu Ile
            340                 345                 350

Thr Ala Asn Pro Val Val Thr Lys Lys Glu Glu Pro Val Asn Ile Glu
        355                 360                 365

Ala Glu Pro Pro Phe Gly Glu Ser Asn Ile Val Ile Gly Ile Gly Asp
    370                 375                 380

Asn Ala Leu Lys Ile Asn Trp Tyr Lys Lys Gly
385                 390                 395

<210> SEQ ID NO 5
<211> LENGTH: 10718
<212> TYPE: DNA
<213> ORGANISM: Dengue virus type 3

<400> SEQUENCE: 5
agttgttagt ctacgtggac cgacaagaac agtttcgact cggaagcttg cttaacgtag    60
tgctaacagt tttttattag agagcagatc tctgatgaac aaccaacgga agaagacggg   120
aaaaccgtct atcaatatgc tgaaacgcgt gagaaaccgt gtgtcaactg gaccacagtt   180
ggcgaagaga ttctcaaaag gactgctgaa cggccaggga ccaatgaaat tggttatggc   240
gttcatagct ttcctcagat ttctagccat tccaccaaca gcaggagtct tggctagatg   300
gggaaccttc aagaagtcgg gagccattaa ggtcctgaaa ggcttcaaga aggagatctc   360
aaacatgctg agcataatca caaacggaaa aagacatcg ctctgtctca tgatgatatt   420
gccagcagca cttgctttcc acttgacttc acgagatgga gagccgcgca tgattgtggg   480
gaagaatgaa agaggaaaat ccctactttt taagacagcc tctggaatta acatgtgcac   540
actcatagcc atggacttgg agagatgtgt gatgacacg gtcacttaca atgcccccca   600
cattaccgaa gtggaacctg aagacattga ctgctggtgc aaccttacat caacatgggt   660
gacttatgga acgtgcaatc aagctggaga gcatagacgc gacaaaagat cagtggcgtt   720
agctcctcat gtcggcatgg gactggacac acgcacccaa acctggatgt cggctgaagg   780
agcttggaga caagtcgaga aggtagagac atgggcctc aggcacccag gttcaccat   840 actagcccta tttcttgccc attacatagg cacttccttg acccgaaagg tggttatttt   900
tatactacta atgctggtca ccccatccat gacaatgaga tgtgtgggaa taggaaacag   960
agattttgtg gaaggtctat caggagctac gtgggttgac gtggtgctcg agcacggggg   1020
gtgtgtgact accatggcta agaacaagcc cacgctggat atagagcttc agaagaccga   1080
ggccacccaa ctggcgaccc taaggaagct atgcattgag gggaaaatta ccaacataac   1140

```
aactgactca agatgtccta cccaagggga agcggttttg cctgaggagc aggaccagaa    1200
ctacgtgtgt aagcatacat acgtagacag aggctggggg aacggttgtg gcttgtttgg    1260
caagggaagc ttggtaacgt gtgcgaaatt tcaatgcctg aaccaatag  agggaaaagt    1320 ggtgcaatat gagaacctca atacaccgt  catcattaca gtgcacacag gagaccaaca    1380
ccaggtagga aatgaaacgc agggagtcac ggctgagata acacctcagg catcaaccac    1440
tgaagccatc ttgcctgaat atggaaccct tgggctagaa tgctcaccac ggacaggttt    1500
ggatttcaat gaaatgatct tactaacaat gaagaacaaa gcatggatgg tacatagaca    1560 atggttttt  gacctacctc taccatggac atcaggagct acaacagaaa cgccaacctg    1620
gaacaggaag gagcttcttg tgacattcaa aaacgcacat gcgaaaaaac aagaagtagt    1680
cgtccttgga tcgcaagagg gagcaatgca taccgcactg acaggagcca cagaaatcca    1740
aaactcagga ggcacaagca tttttgcggg gcacttaaaa tgtagactta agatggacaa    1800
attggaactc aaggggatga gctatgcaat gtgcacgaat accttgtgt  tgaagaaaga    1860 agtctcagaa acgcagcatg gacaatact  cattaaggtc gagtacaagg gggaagatgc    1920
gccttgcaag attcctttct ccacagagga tggacaaggg aaagctcaca atggcagact    1980
gatcacagcc aacccagtgg tgactaagaa ggaggagcct gtcaatattg aggctgaacc    2040
tccttttggg gaaagtaata tagtaattgg aattggagac aacgccttga aaatcaactg    2100
gtacaagaag ggaagctcta ttgggaagat gttcgaggcc actgccagag gtgcaaggcg    2160
catggccatc ttgggagaca cagcttggga cttttggatca gtgggtggtg ttctgaactc    2220
attaggcaaa atggtgcacc aaatattcgg aagtgcttac acagccctat tcagtggagt    2280
ctcttgggtg atgaaaattg gaataggtgt tctcttgact tggatagggt tgaattcaaa    2340
aaacacatcc atgtcatttt catgcattgc gataggaatc attacactct atctgggagc    2400
tgtggtacaa gctgacatgg ggtgtgtcat aaactggaaa ggcaaagaac tcaaatgtgg    2460
aagtggaatt ttcgtcacca acgaggtcca tacctggaca gagcaataca attccaagc     2520 agactcccca aaaagattgg cgacagccat tgcaggcgct tgggagaatg gagtgtgcgg    2580
aattaggtca acaaccagaa tggagaatct cctgtggaag caaatagcca atgaactgaa    2640
ctacatatta tgggaaaaca atatcaaatt aacggtagtt gtgggcgata caattggggt    2700
cttagagcaa ggaaaagaa  cactaacacc acaacccatg gagctaaaat actcatggaa    2760
aacatgggga aaggcaaaaa tagtgacagc tgaaacacaa aattcctcct tcataataga    2820
cgggccaaac acaccggagt gtccaagtgc ctcaagagca tggaatgtgt gggaggtgga    2880
agattacggg ttcggagtct tcacaaccaa catatggctg aaactccgag atgtgtacac    2940
ccaactatgt gaccataggc taatgtcggc agccgtcaag gatgagaggg ccgtacacgc    3000
cgacatgggc tattggatag aaagccaaaa gaatggaagt tggaagctag aaaaagcatc    3060
cctcatagag gtgaaaacct gcacatggcc aaaatcacac actctttgga gcaatggtgt    3120
gctagagagt gacatgatca tcccaaagag cctcgctggc cctatttcgc aacacaacta    3180
caggcctggg taccacaccc aaacagcagg accctggcac ttaggaaaat tggagctgga    3240
cttcaactat tgtgaaggaa caacagttgt catcacagaa aactgtggga caagaggcc     3300 atcattgaga acaacaacag tgtcaggaa  gttgatacac gaatggtgtt gccgctcgtg    3360
cacacttcct cccctgcgat acatgggaga agacggctgc tggtatggca tggaaatcag    3420
acccatcagt gagaaagaag agaacatggt aaagtcttta gtctcagcgg gaagtggaaa    3480
```

-continued

```
ggtggacaac ttcacaatgg gtgtcttgtg tttggcaatc ctctttgaag aggtgatgag   3540
aggaaaattt gggaagaaac acatgattgc aggggttctc ttcacgtttg tgctccttct   3600
ctcagggcaa ataacatgga gagacatggc gcacacacta ataatgattg ggtccaacgc   3660
ctctgacagg atgggaatgg gcgtcaccta cctagcttta attgcaacat ttaaaatcca   3720
gccattcttg gctttgggat ttttcctaag aaaactgaca tctagagaaa atttattgtt   3780
aggagttggg ctggctatgg caacaacgtt acaactgcca gaggacattg aacaaatggc   3840
aaatggaatc gctctggggc tcatggctct taaactgata acacaatttg aaacatacca   3900
attatggacg gcattagtct ccttaacgtg ttcaaataca attcttacgt tgactgttgc   3960
ctggagaaca gccacccctga ttttggccgg agtttcgctt ttaccagtgt gccagtcttc   4020
gagcatgagg aaaacagact ggcttccaat gacagtggca gctatgggag ttccacccct   4080 accactttt attttttagct tgaaagacac actcaaaagg agaagctggc cactgaatga   4140
aggggtgatg gctgttgggc ttgtgagcat tctggccagt tctctcctta gaaatgatgt   4200
gcccatggct ggaccattag tggccggggg cttgctgata gcgtgctacg tcataactgg   4260
cacgtcagca gacctcactg tggaaaaagc agcagatgta acatgggagg aagaggctga   4320
gcaaacagga gtgtcccaca acttaatgat cacagttgat gatgatgaa caatgagaat   4380 aaaagatgat gagactgaga acatcctaac agtgctttta aaaacagcat tactaatagt   4440
atcaggcatc tttccatact ccatacccgc aacattgttg gtctggcata cttggcagaa   4500
gcaaacccaa aggtccggcg ttctgtggga cgtacccagc cccccagaga cacagaaagc   4560
agaactggaa gaagggtttt ataggatcaa acagcaagga attcttggga aacccaagt   4620 aggggttgga gtacagaaag aaggagtctt ccacaccatg tggcacgtca agagggggc   4680 agtgttgaca cataatggga aaagactgga accaaactgg gctagcgtga aaaagatct   4740 gatttcatac ggaggaggat ggagattgag cgcgcaatgg caaaggggg aggaggtgca   4800 ggttattgcc gtggagcctg ggaagaaccc aaagaacttt caaaccatgc caggcacttt   4860
tcagactaca acagggaaa taggagcaat tgcactggat ttcaagcctg aacttcagg   4920 atctcctatc ataaacagag agggaaaggt agtgggactg tatggcaatg gagtggttac   4980
aaagaatggt ggctacgtca gcggaatagc gcaaacaaat gcagaaccag atggaccgac   5040
accagagttg gaagaagaga tgttcaaaaa gcgaaatcta accataatgg atcttcatcc   5100
tgggtcagga aagacacgga aataccttcc agctattgtt agagaggcaa tcaagagacg   5160
tttaagaact ctaattttgg caccgacaag ggtggttgca gctgagatgg aagaagcatt   5220
gaaagggctc ccaataaggt accaaacaac agcaacaaaa tctgaacaca caggaagaga   5280
gattgttgat ctaatgtgcc acgcaacgtt cacaatgcgc ttgctgtcac cagttagggt   5340
tccaaattat aacttgataa taatggatga ggcccatttc acagacccag ccagcatagc   5400
ggctagaggg tacatatcaa ctcgtgttgg aatgggagag gcagccgcaa ttttcatgac   5460
agcaacgccc cctggaacag ctgatgcctt tcctcagagc aacgctccaa ttcaagatga   5520
agaaagggac ataccagaac gctcatggaa ttcaggcaat gaatggatta ccgacttcgc   5580
tgggaaaacg gtgtggtttg tccccagcat taaagccgga aatgacatag caaactgctt   5640
gcggaaaaac ggaaaaaagg tcattcaact tagtaggaag acttttgaca cagaatatca   5700
gaagactaaa ctgaatgatt gggacttcgt ggtgacaact gacatttcag aaatgggggc   5760
caatttcaaa gcagatagag tgatcgaccc aagaagatgt ctcaaaccag tgatcctgac   5820
agatggacca gagcgggtga tcctggctgg accaatgcca gtcaccgcgg cgagtgctgc   5880
```

-continued

```
gcaaaggaga ggaagagttg gcaggaaccc acaaaaagaa aatgaccagt acatattcac    5940
gggccagcct ctcaacaatg atgaagacca tgctcactgg acagaagcaa aaatgctgct    6000
ggacaacatt aacacaccag aagggattat accagctctc tttgaaccag aaagggagaa    6060
gtcagccgcc atagacggtg agtatcgcct gaagggtgag tccaggaaga ctttcgtgga    6120
actcatgagg aggggtgacc ttccagtttg gttagcccat aaagtagcat cagaagggat    6180
caaatataca gatagaaaat ggtgctttga tggacaacgc aataatcaaa ttttagagga    6240
gaacatggat gtggaaatct ggacaaagga aggagaaaag aaaaaattga gacctaggtg    6300
gcttgatgcc cgcacttatt cagatccctt agcactcaag gaatttaagg actttgcggc    6360
tggcagaaag tcaatcgccc ttgatcttgt gacagaaata ggaagagtgc cttcacacct    6420
agcccacaga acgagaaacg ctctggacaa tctggtgatg ctgcatacgt cagaacatgg    6480
cggtagggcc tacaggcatg cggtggagga actaccagaa acaatggaaa cacttttact    6540
cttgggactc atgatcttgt tgacaggtgg agcaatgctt ttcttgatat caggaaaagg    6600
gattggaaag acttcaatag gactcatttg tgtaattgcc tccagcggca tgttgtggat    6660
ggccgaaatc ccactccagt ggatcgcgtc ggctatagtc ctggagtttt ttatgatggt    6720
gttgcttata ccagaaccag aaaagcagag acccccccaa gacaaccaac tcgcatatgt    6780
cgtgataggc atacttacat tggctgcaat aatagcagcc aatgaaatgg gactgttgga    6840
aactacaaag agagatttag gaatgtctaa ggagccaggt gttgtttctc aaccagcta    6900 tttggatgtg gacttgcacc cagcatcagc ctggacattg tacgccgtgg ccactacagt    6960
aataacacca atgttaagac ataccataga gaattctaca gcaaatgtgt ccctggcagc    7020
tatagccaac caggcagtgg tcctgatggg tttggacaaa ggatggccaa tatcaaaaat    7080
ggacttaggc gtaccactac tggcattggg ttgctattca caagtgaacc cactgactct    7140
aacagcggca gtacttttgc taatcacaca ttatgctatt ataggtccag gattgcaggc    7200
aaaagccact cgtgaagctc agaaaaggac agctgctgga ataatgaaga tccaacggt    7260 ggatgggata atgacaatag acctagatcc tgtaatatat gattcaaaat ttgaaaagca    7320
actgggacag gttatgctcc tggttttgtg tgcagttcaa cttttgttaa tgagaacatc    7380
atgggccttg tgtgaagctt taactctagc tacaggacca ataacaacac tctgggaagg    7440
atcacctgga aagttttgga acaccacgat agctgtttcc atggcgaaca tttttagagg    7500
gagctattta gcaggagctg ggcttgcttt tctattatg aaatcagttg gaacaggaaa    7560
aagaggaaca ggttcacaag gcgaaacttt aggagaaaaa tggaaaaaga attaaatca    7620 attatcccgg aaagagtttg acctttacaa gaaatctgga atcactgaag tggatagaac    7680
agaagccaaa gaagggttga aaagaggaga ataacacat catgccgtgt ccagaggtag    7740
cgcaaaactt caatggtttg tggagagaaa catggtcatt cccgaaggaa gagtcataga    7800
cttgggctgt ggaagaggag gctggtcata ctactgtgca ggactgaaaa aagtcacaga    7860
agtgcgagga tacacaaaag gcggtccagg acacgaagaa ccagtaccta tgtctacata    7920
tggatggaac atagttaagt taatgagtgg aaaggatgtg ttttatcttc cacctgaaaa    7980
gtgtgatacc ctgttgtgtg acatcggaga atcttcacca gcccaacag tggaagaaag    8040 cagaactata agagttttga gatggttga accatggcta aaaacaacc agttttgcat    8100 taaagtattg aaccctacaa tgccaactgt gattgagcac ctagaaagac tacaaaggaa    8160
acatggagga atgcttgtga gaaatccact ttcacgaaac tccacgcacg aaatgtactg    8220
```

-continued

```
gatatctaat ggcacaggta acattgtctc ttcagtcaac atggtatcta gattgctact    8280
gaacaggttc acgatgacac acaggagacc taccatagag aaagatgtgg atttaggagc    8340
aggaactcga catgttaatg cggaaccaga acacccaac atggatgtca ttggggaaag     8400
aataaaaagg atcaaggagg agcacaattc aacatggcac tatgatgacg aaaaccccta    8460
caaaacgtgg gcttaccacg gatcctatga agtcaaagcc acaggctcag cctcctccat    8520
gataaatgga gtcgtgaaac tcctcactaa accatgggag gtggtgccca tggtgacaca    8580
gatggcaatg acagatacaa ctccatttgg ccagcagaga gtctttaaag agaaagtgga    8640
caccaggaca cccaggccca tgccagggac aagaaaggtt atggggatca cagcggagtg    8700
gctctggaga accctgggaa ggaacaaaag acccaggtta tgcacaaggg aagagtttac    8760
aaaaaaggtc agaactaacg cagccatggg cgccgttttc acagaggaga accaatggga    8820
cagtgcgaaa gctgctgttg aggatgaaga attttggaaa cttgtggaca gagaacgtga    8880
actccacaaa ttgggcaagt gtggaagctg tgtttacaac atgatgggca agagagagaa    8940
gaaacttgga gagtttggca aagcaaaagg cagtagagct atatggtaca tgtggttggg    9000
agccaggtac cttgagttcg aagcccttgg attcctaaat gaagaccact ggttctcgcg    9060
tgacaactct tacagtggag tagaaggaga aggactgcac aagctaggct acatattaag    9120
ggacatttcc aagataccgg gaggagctat gtatgctgat gacacagctg gttgggacac    9180
aagaataaca gaagatgacc tgcacaatga ggaaaagatc acacagcaaa tggaccctga    9240
acacaggcag ttagcgaacg ctatatttaa gctcacatac caaaacaaag tggtcaaagt    9300
tcaacgaccg actccaacgg gcacggtaat ggacatcata tctaggaaag accaaagagg    9360
cagtggacag gtgggaactt atggtctgaa tacattcacc aacatggaag tccagttagt    9420
cagacaaatg gaaggagaag gtgtgctgtc aaaggcagac tcgagaacc tcatctgcc      9480
agagaagaaa attacacaat ggttggaaac caaggagtg gagaggttaa aaagaatggc     9540
cattagcggg gatgattgtg tagtgaaacc aatcgatgac aggttcgcta atgccctgct    9600
tgctctgaac gatatgggaa aggttcggaa agacatacct caatggcagc catcaaaggg    9660
atggcatgat tggcaacagg ttcctttctg ctcccaccac tttcatgaat tgatcatgaa    9720
agatggaaga aagttagtgg ttccctgtag accccaggac gaactaatag gaagagcaag    9780
aatctctcaa ggagcgggat ggagccttag agagaccgca tgtctgggga agcctacgc     9840
tcaaatgtgg agtctcatgt actttcacag aagagatctc agactagcat ccaacgccat    9900
atgttcagca gtaccagtcc actgggtccc cacaagtaga acgacatggt ctattcatgc    9960
tcaccatcag tggatgacta cagaagacat gcttactgtc tggaacaggg tgtggatcga   10020
ggacaatcca tggatggaag acaaaactcc agttacaacc tgggaaaatg ttccatatct   10080
agggaagaga gaagaccaat ggtgcggatc acttattggt ctcacctcca gagcaacctg   10140
ggcccagaac atacccacag caattcaaca ggtgagaagt cttataggga atgaagagtt   10200
tctggattac atgccttcaa tgaagagatt caggaaggag gaggagtcgg aaggagccat   10260
ttggtaaacg taggaagtga aaaagaggca aactgtcagg ccaccttaag ccacagtacg   10320
gaagaagctg tgctgcctgt gagccccgtc aaggacgtt aaaagaagaa gtcaggcccc    10380
aaagccacgg tttgagcaaa ccgtgctgcc tgtagctccg tcgtggggac gtaaaacctg   10440
ggaggctgca aactgtggaa gctgtacgca cggtgtagca gactagcggt tagaggagac   10500
ccctcccatg acacaacgca gcagcggggc ccgagcactg agggaagctg tacctccttg   10560
caaaggacta gaggttagag gagacccccc gcaaacaaaa acagcatatt gacgctggga   10620
```

```
gagaccagag atcctgctgt ctcctcagca tcattccagg cacagaacgc cagaaaatgg    10680
aatggtgctg ttgaatcaac aggttcttaa aagagacg                           10718

<210> SEQ ID NO 6
<211> LENGTH: 10746
<212> TYPE: DNA
<213> ORGANISM: Dengue virus type 1

<400> SEQUENCE: 6
agttgttagt ctacgtggac cgacaagaac agtttcgaat cggaagcttg cttaacgtag      60
ttctaacagt tttttattag agagcagatc tctgatgaac aaccaacgga aaaagacggg     120
tcgaccgtct ttcaatatgc tgaaacgcgc gagaaaccgc gtgtcaactg tttcacagtt     180
ggcgaagaga ttctcaaaag gattgctttc aggccaagga cccatgaaat tggtgatggc     240
ttttatagca ttcctaagat ttctagccat acctccaaca gcaggaattt tggctagatg     300
gggctcattc aagaagaatg gagcgatcaa agtgttacgg ggtttcaaga agaaatctc     360 aaacatgttg aacataatga caggaggaa aagatctgtg accatgctcc tcatgctgct     420
gcccacagcc ctggcgttcc atctgaccac ccgaggggga gagccgcaca tgatagttag     480
caagcaggaa agaggaaaat cacttttgtt taagacctct gcaggtgtca acatgtgcac     540
ccttattgca atggatttgg gagagttatg tgaggacaca atgacctaca aatgcccccg     600
gatcactgag acggaaccag atgacgttga ctgttggtgc aatgccacgg agacatgggt     660
gacctatgga acatgttctc aaactggtga acaccgacga gacaaacgtt ccgtcgcact     720
ggcaccacac gtagggcttg gtctagaaac aagaaccgaa acgtggatgt cctctgaagg     780
cgcttggaaa caaatacaaa aagtggagac ctgggctctg agacacccag gattcacggt     840
gatagccctt tttctagcac atgccatagg aacatccatc acccagaaag ggatcatttt     900
tattttgctg atgctggtaa ctccatccat ggccatgcgg tgcgtgggaa taggcaacag     960
agacttcgtg gaaggactgt caggagctac gtgggtggat gtggtactgg agcatggaag    1020
ttgcgtcact accatggcaa agacaaaacc aacactggac attgaactct tgaagacgga    1080
ggtcacaaac cctgccgtcc tgcgcaaact gtgcattgaa gctaaaatat caacaccac    1140 caccgattcg agatgtccaa cacaaggaga agccacgctg gtggaagaac aggacacgaa    1200
ctttgtgtgt cgacgaacgt tcgtggacag aggctgggc aatggttgtg gctattcgg    1260 aaaaggtagc ttaataacgt gtgctaagtt taagtgtgtg acaaaactgg aaggaaagat    1320
agtccaatat gaaaacttaa atatttcagt gatagtcacc gtacacactg agaccagca    1380 ccaagttgga aatgagacca cagaacatgg acaattgca accataacac ctcaagctcc    1440
cacgtcggaa atacagctga cagactacga agctctaaca ttggattgtt cacctagaac    1500
agggctagac tttaatgaga tggtgttgtt gacaatgaaa aaaaatcat ggctcgtcca    1560 caaacaatgg tttctagact taccactgcc ttggacctcg ggggcttcaa catcccaaga    1620
gacttggaat agacaagact tgctggtcac atttaagaca gctcatgcaa aaaagcagga    1680
agtagtcgta ctaggatcac aagaaggagc aatgcacact gcgttgactg gagcgacaga    1740
aatccaaacg tctggaacga caacaatttt tgcaggacac ctgaaatgca gactaaaaat    1800
ggataaactg actttaaaag ggatgtcata tgtaatgtgc acagggtcat tcaagttaga    1860
gaaggaagtg gctgagaccc agcatggaac tgttctagtg caggttaaat acgaaggaac    1920
agatgcacca tgcaagatcc ccttctcgtc ccaagatgag aagggagtaa cccagaatgg    1980
```

```
gagattgata acagccaacc ccatagtcac tgacaaagaa aaaccagtca acattgaagc    2040
ggagccacct tttggtgaga gctacattgt ggtaggagca ggtgaaaaag ctttgaaact    2100
aagctggttc aagaagggaa gcagtatagg gaaaatgttt gaagcaactg cccgtggagc    2160
acgaaggatg gccatcctgg gagacactgc atgggacttc ggttctatag gaggggtgtt    2220
cacgtctgtg ggaaaactga tacaccagat ttttgggact gcgtatggag ttttgttcag    2280
cggtgtttct tggaccatga agataggaat agggattctg ctgacatggc taggattaaa    2340
ctcaaggagc acgtcccttt caatgacgtg tatcgcagtt ggcatggtca cgctgtacct    2400
aggagtcatg gttcaggcgg actcgggatg tgtaatcaac tggaaaggca gagaactcaa    2460
atgtggaagc ggcattttg tcaccaatga agtccacacc tggacagagc aatataaatt     2520
ccaggccgac tcccctaaga gactatcagc ggccattggg aaggcatggg aggagggtgt    2580
gtgtggaatt cgatcagcca ctcgtctcga gaacatcatg tggaagcaaa tatcaaatga    2640
attaaaccac atcttacttg aaaatgacat gaaatttaca gtggtcgtag agacgttag     2700 tggaatcttg gcccaaggaa agaaaatgat taggccacaa cccatggaac acaaatactc    2760
gtggaaaagc tggggaaaag ccaaaatcat aggagcagat gtacagaata ccaccttcat    2820
catcgacggc ccaaacaccc cagaatgccc tgataaccaa agagcatgga acatttggga    2880
agttgaagac tatggatttg gaattttcac gacaaacata tggttgaaat tgcgtgactc    2940
ctacactcaa gtgtgtgacc accggctaat gtcagctgcc atcaaggata gcaaagcagt    3000
ccatgctgac atggggtatt ggatagaaag tgaaagaaac gagacttgga agttggcaag    3060
agcctccttc atagaagtta agacatgcat ctggccaaaa tcccacactc tatggagcaa    3120
tggagtcctg gaaagtgaga tgataatccc aaagatatat ggaggaccaa tatctcagca    3180
caactacaga ccaggatatt tcacacaaac agcagggccg tggcacttgg gcaagttaga    3240
actagatttt gatttatgtg aaggtaccac tgttgttgtg gatgaacatt gtggaaatcg    3300
aggaccatct cttagaacca caacagtcac aggaaagaca atccatgaat ggtgctgtag    3360
atcttgcacg ttaccccccc tacgtttcaa aggagaagac gggtgctggt acggcatgga    3420
aatcagacca gtcaaggaga aggaagagaa cctagttaag tcaatggtct ctgcagggtc    3480
aggagaagtg gacagttttt cactaggact gctatgcata tcaataatga tcgaagaggt    3540
aatgagatcc agatggagca gaaaaatgct gatgactgga acattggctg tgttcctcct    3600
tcttacaatg ggacaattga catggaatga tctgatcagg ctatgtatca tggttggagc    3660
caacgcttca gacaagatgg ggatgggaac aacgtaccta gctttgatgg ccactttcag    3720
aatgagacca atgttcgcag tcgggctact gtttcgcaga ttaacatcta gagaagttct    3780
tcttcttaca gttggattga gtctggtggc atctgtagaa ctaccaaatt ccttaggaga    3840 gctagggat ggacttgcaa tggcatcat gatgttgaaa ttactgactg attttcagtc     3900
acatcagcta tgggctacct tgctgtcttt aacatttgtc aaaacaactt tttcattgca    3960
ctatgcatgg aagacaatgg ctatgatact gtcaattgta tctctcttcc ctttatgcct    4020
gtccacgact tctcaaaaaa caacatggct tccggtgttg ctgggatctc ttggatgcaa    4080
accactaacc atgtttctta acagaaaaa caaaatctgg ggaaggaaaa gctggcctct    4140
caatgaagga attatggctg ttggaatagt tagcattctt ctaagttcac ttctcaagaa    4200
tgatgtgcca ctagctggcc cactaatagc tggaggcatg ctaatagcat gttatgtcat    4260
atctggaagc tcggccgatt tatcactgga gaaagcggct gaggtctcct gggaagaaga    4320
agcagaacac tctggtgcct cacacaacat actagtggag gtccaagatg atggaaccat    4380
```

```
gaagataaag gatgaagaga gagatgacac actcaccatt ctcctcaaag caactctgct    4440
agcaatctca ggggtatacc caatgtcaat accggcgacc ctctttgtgt ggtattttg     4500 gcagaaaaag aaacagagat caggagtgct atgggacaca cccagccctc cagaagtgga    4560
aagagcagtc cttgatgatg gcatttatag aattctccaa agaggattgt tgggcaggtc    4620
tcaagtagga gtaggagttt ttcaagaagg cgtgttccac acaatgtggc acgtcaccag    4680
gggagctgtc ctcatgtacc aagggaagag actggaacca agttgggcca gtgtcaaaaa    4740
agacttgatc tcatatggag gaggttggag gtttcaagga tcctggaacg cgggagaaga    4800
agtgcaggtg attgctgttg aaccggggaa gaaccccaaa aatgtacaga cagcgccggg    4860
taccttcaag accoctgaag gcgaagttgg agccatagct ctagactta aacccggcac     4920 atctggatct cctatcgtga acagagaggg aaaaatagta ggtctttatg gaaatggagt    4980
ggtgacaaca agtggtacct acgtcagtgc catagctcaa gctaaagcat cacaagaagg    5040
gcctctacca gagattgagg acgaggtgtt taggaaaaga aacttaacaa taatggacct    5100
acatccagga tcgggaaaaa caagaagata ccttccagcc atagtccgtg aggccataaa    5160
aagaaagctg cgcacgctag tcttagctcc cacaagagtt gtcgcttctg aaatggcaga    5220
ggcgctcaag ggaatgccaa taaggtatca gacaacagca gtgaagagtg aacacacggg    5280
aaaggagata gttgacctta tgtgtcacgc cactttcact atgcgtctcc tgtctcctgt    5340
gagagttccc aattataata tgattatcat ggatgaagca catttcaccg atccagccag    5400
catagcagcc agagggtata tctcaacccg agtgggtatg ggtgaagcag ctgcgatttt    5460
catgacagcc actccccccg gatcggtgga ggcctttcca cagagcaatg cagttatcca    5520
agatgaggaa agagacattc ctgaaagatc atggaactca ggctatgact ggatcactga    5580
tttcccaggt aaaacagtct ggtttgttcc aagcatcaaa tcaggaaatg acattgccaa    5640
ctgtttaaga aagaatggga aacgggtggt ccaattgagc agaaaaactt ttgacactga    5700
gtaccagaaa acaaaaaata cgactgggga ctatgttgtc acaacagaca tatccgaaat    5760
gggagcaaac ttccgagccg acagggtaat agacccgagg cggtgcctga accggtaat    5820 actaaaagat ggcccagagc gtgtcattct agccggaccg atgccagtga ctgtggctag    5880
cgccgcccag aggagaggaa gaattggaag gaaccaaaat aaggaaggcg atcagtatat    5940
ttacatggga cagcctctaa acaatgatga ggaccacgcc cattggacag aagcaaaaat    6000
gctccttgac aacataaaca caccagaagg gattatccca gccctctttg agccggagag    6060
agaaaagagt gcagcaatag acgggggaata cagactacgg ggtgaagcga ggaaaacgtt    6120
cgtggagctc atgagaagag agatttacc tgtctggcta tcctacaaag ttgcctcaga    6180
aggcttccag tactccgaca aaggtgtgt ctttgatggg gaaaggaaca ccaggtgtt    6240 ggaggagaac atggacgtgg agatctggac aaaagaagga gaaagaaaga aactacgacc    6300
ccgctggctg gatgccagaa catactctga cccactggct ctgcgcgaat caaagagtt    6360 cgcagcagga agaagaagcg tctcaggtga cctaatatta gaaatagga acttccaca    6420 acatttaacg caaaggcccc agaacgcctt ggacaatctg gttatgttgc acaactctga    6480
acaaggagga aaagcctata gacacgccat ggaagaacta ccagacacca tagagacgtt    6540
aatgctccta gctttgatag ctgtgctgac tggtggagtg acgttgttct tcctatcagg    6600
aaggggtcta ggaaaaacat ccattggcct actctgcgtg attgcctcaa gtgcactgtt    6660
atggatggcc agtgtggaac cccattggat agcggcctct atcatactgg agttcttct    6720
```

```
gatggtgttg cttattccag agccggacag acagcgcact ccacaagaca accagctagc    6780
atacgtggtg ataggtctgt tattcatgat attgacagtg gcagccaatg agatgggatt    6840
actggaaacc acaaagaagg acctggggat tggtcatgca gctgctgaaa accaccatca    6900
tgctgcaatc ctggacgtag acctacatcc agcttcagcc tggactctct atgcagtggc    6960
cacaacaatt atcactccca tgatgagaca cacaattgaa aacacaacgg cgaatatttc    7020
cctgacagct attgcaaacc aggcagctat attgatggga cttgacaagg gatggccaat    7080
atcaaagatg gacataggag ttccacttct cgccttgggg tgctattctc aggtgaaccc    7140
gctgacgctg acagcggcgg tatttatgct agtggctcat tatgccataa ttggacccgg    7200
actgcaagca aaagctacta gagaagctca aaaaaggaca gcagccggaa taatgaaaaa    7260
cccaactgtc gacgggatcg ttgcaataga tttggaccct gtggtttacg atgcaaaatt    7320
tgaaaaacag ctaggccaaa taatgttgtt gatactttgc acatcacaga tcctcctgat    7380
gcggaccaca tgggccttgt gtgaatccat cacactagcc actggacctc tgactacgct    7440
ttgggaggga tctccaggaa aattctggaa caccacgata gcggtgtcca tggcaaacat    7500
ttttagggga agttatctag caggagcagg tctggccttt tcattaatga aatctctagg    7560
aggaggtagg agaggcacgg gagcccaagg ggaaacactg ggagaaaaat ggaaaagaca    7620
gctaaaccaa ttgagcaagt cagaattcaa cacttacaaa aggagtggga ttatagaggt    7680
ggatagatct gaagccaaag aggggttaaa aagaggagaa acgactaaac acgcagtgtc    7740
gagaggaacg gccaaactga ggtggtttgt ggagaggaac cttgtgaaac cagaagggaa    7800
agtcatagac ctcggttgtg gaagaggtgg ctggtcatat tattgcgctg ggctgaagaa    7860
agtcacagaa gtgaaaggat acacgaaagg aggacctgga catgaggaac caatcccaat    7920
ggcaacctat ggatggaacc tagtaaagct atactccggg aaagatgtat tctttacacc    7980
acctgagaaa tgtgacaccc tcttgtgtga tattggtgag tcctctccga acccaactat    8040
agaagaagga gagaacgttac gtgttctaaa gatggtggaa ccatggctca gaggaaacca    8100
attttgcata aaaattctaa atccctatat gccgagtgtg gtagaaactt tggagcaaat    8160
gcaaagaaaa catggaggaa tgctagtgcg aaatccactc tcaagaaact ccactcatga    8220
aatgtactgg gtttcatgtg gaacaggaaa cattgtgtca gcagtaaaca tgacatctag    8280
aatgctgcta aatcgattca atggctcac aggaagcca acatatgaaa gagacgtgga    8340
cttaggcgct ggaacaagac atgtggcagt agaaccagag gtggccaacc tagatatcat    8400
tggccagagg atagagaata taaaaaatga acacaaatca acatggcatt atgatgagga    8460
caatccatac aaaacatggg cctatcatgg atcatatgag gtcaagccat caggatcagc    8520
ctcatccatg gtcaatggtg tggtgagact gctaaccaaa ccatgggatg tcattcccat    8580
ggtcacacaa atagccatga ctgacaccac accctttgga caacagaggg tgtttaaaga    8640
gaaagttgac acgcgtacac caaagcgaa acgaggcaca gcacaaatta tggaggtgac    8700
agccaggtgg ttatggggtt ttctctctag aaacaaaaaa cccagaatct gcacaagaga    8760
ggagttcaca agaaaagtca ggtcaaacgc agctattgga gcagtgttcg tcgatgaaaa    8820
tcaatggaac tcagcaaaag aggcagtgga agatgaacgg ttctgggacc ttgtgcacag    8880
agagagggag cttcataaac aaggaaaatg tgccacgtgt gtctacaaca tgatgggaaa    8940
gagagagaaa aaattaggag agttcggaaa ggcaaaagga agtcgcgcaa tatggtacat    9000
gtggttggga gcgcgctttt tagagtttga agcccttggt ttcatgaatg aagatcactg    9060
gttcagcaga gagaattcac tcagtggagt ggaaggagaa ggactccaca aacttggata    9120
```

```
catactcaga gacatatcaa agattccagg gggaaatatg tatgcagatg acacagccgg    9180
atgggacaca agaataacag aggatgatct tcagaatgag gccaaaatca ctgacatcat    9240
ggaacctgaa catgccctat tggccacgtc aatctttaag ctaacctacc aaaacaaggt    9300
agtaagggtg cagagaccag cgaaaaatgg aaccgtgatg gatgtcatat ccagacgtga    9360
ccagagagga agtggacagg ttggaaccta tggcttaaac accttcacca acatggaggc    9420
ccaactaata agacaaatgg agtctgaggg aatcttttca cccagcgaat tggaaacccc    9480
aaatctagcc gaaagagtcc tcgactggtt gaaaaaacat ggcaccgaga ggctgaaaag    9540
aatggcaatc agtggagatg actgtgtggt gaaaccaatt gatgacagat ttgcaacagc    9600
cttaacagct ttgaatgaca tgggaaaggt aagaaaagac ataccgcaat gggaaccttc    9660
aaaaggatgg aatgattggc aacaagtgcc tttctgttca caccatttcc accagctgat    9720
tatgaaggat gggagggaga tagtggtgcc atgccgcaac caagatgaac ttgtaggtag    9780
ggccagagta tcacaaggcg ccggatggag cttgagagaa actgcatgcc taggcaagtc    9840
atatgcacaa atgtggcagc tgatgtactt ccacaggaga gacttgagat tagcggctaa    9900
tgctatctgt tcagccgttc cagttgattg ggtcccaacc agccgtacca cctggtcgat    9960
ccatgcccac catcaatgga tgacaacaga agacatgttg tcagtgtgga atagggtttg   10020
gatagaggaa aacccatgga tggaggacaa gactcatgtg tccagttggg aagacgttcc   10080
atacctagga aaaagggaag atcaatggtg tggatcccta ataggcttaa cagcacgagc   10140
cacctgggcc accaacatac aagtggccat aaaccaagtg agaaggctca ttgggaatga   10200
gaattatcta gacttcatga catcaatgaa gagattcaaa aacgagagtg atcccgaagg   10260
ggcactctgg taagccaact cattcacaaa ataaaggaaa ataaaaaatc aaacaaggca   10320
agaagtcagg ccggattaag ccatagcacg gtaagagcta tgctgcctgt gagccccgtc   10380
caaggacgta aaatgaagtc aggccgaaag ccacggttcg agcaagccgt gctgcctgta   10440
gctccatcgt ggggatgtaa aaacccggga ggctgcaaac catggaagct gtacgcatgg   10500
ggtagcagac tagtggttag aggagacccc tcccaagaca caacgcagca gcggggccca   10560
acaccagggg aagctgtacc ctggtggtaa ggactagagg ttagaggaga ccccccgcac   10620
aacaacaaac agcatattga cgctgggaga gaccagagat cctgctgtct ctacagcatc   10680
attccaggca cagaacgcca gaaaatggaa tggtgctgtt gaatcaacag gttctaaacg   10740
aagagc                                                              10746
```